US009396505B2

(12) United States Patent
Herrold et al.

(10) Patent No.: US 9,396,505 B2
(45) Date of Patent: Jul. 19, 2016

(54) CAREGIVER INTERFACE FOR ELECTRONIC MEDICAL RECORDS

(75) Inventors: Edmund M. Herrold, New York, NY (US); David A. Polivka, Bluemont, VA (US)

(73) Assignee: Medicomp Systems, Inc., Chantilly, VA (US)

( * ) Notice: Subject to any disclaimer, the term of this patent is extended or adjusted under 35 U.S.C. 154(b) by 116 days.

(21) Appl. No.: 12/817,050

(22) Filed: Jun. 16, 2010

(65) Prior Publication Data

US 2011/0004847 A1 Jan. 6, 2011

Related U.S. Application Data

(60) Provisional application No. 61/187,609, filed on Jun. 16, 2009.

(51) Int. Cl.
*G06F 3/048* (2013.01)
*G06Q 50/22* (2012.01)
*G06F 19/00* (2011.01)
*G06Q 10/10* (2012.01)

(52) U.S. Cl.
CPC .............. *G06Q 50/22* (2013.01); *G06F 19/322* (2013.01); *G06Q 10/10* (2013.01); *G06F 19/3406* (2013.01); *G06F 19/3487* (2013.01); *G06F 19/363* (2013.01)

(58) Field of Classification Search
CPC ................................ G06F 19/324; G06F 19/32
See application file for complete search history.

(56) References Cited

U.S. PATENT DOCUMENTS

| 5,924,074 | A | * | 7/1999 | Evans | 705/3 |
| 2006/0080140 | A1 | | 4/2006 | Buttner et al. | |
| 2006/0206361 | A1 | * | 9/2006 | Logan, Jr. | 705/3 |
| 2006/0241977 | A1 | * | 10/2006 | Fitzgerald et al. | 705/3 |
| 2007/0088525 | A1 | | 4/2007 | Fotiades et al. | |
| 2007/0165049 | A1 | | 7/2007 | Murawski et al. | |
| 2009/0024411 | A1 | * | 1/2009 | Albro et al. | 705/2 |
| 2009/0198514 | A1 | * | 8/2009 | Rhodes | 705/3 |

FOREIGN PATENT DOCUMENTS

| GB | 2 389 290 A | 12/2003 |
| WO | WO 01/80117 A1 | 10/2001 |

OTHER PUBLICATIONS

International Search Report and Written Opinion mailed Jul. 27, 2012.

* cited by examiner

*Primary Examiner* — Jeffrey A Gaffin
*Assistant Examiner* — Ayesha Huertas Torres
(74) *Attorney, Agent, or Firm* — Merchant & Gould, P.C.

(57) ABSTRACT

A caregiver user interface displays information from a patient's electronic medical record. The interface associates medical records together that include a common data item. The interface also displays information about data items, such as the status of a data item in an associated historical record. Controls can be displayed in the user interface, which are linked to the historical records.

20 Claims, 20 Drawing Sheets

FIG. 18

CAREGIVER INTERFACE FOR ELECTRONIC MEDICAL RECORDS

CROSS REFERENCE TO RELATED APPLICATION

This application claims priority to U.S. Provisional Application Ser. No. 61/187,609, filed on Jun. 16, 2009, entitled CAREGIVER INTERFACE FOR ELECTRONIC MEDICAL RECORDS, the disclosure of which is incorporated by reference herein in its entirety.

TECHNICAL FIELD

The present disclosure relates to electronic medical records, and more particularly to a caregiver interface for electronic medical records.

BACKGROUND

When a caregiver interacts with a patient, the caregiver often makes a record of the findings from that interaction in a patient note. For example, the caregiver might record in the patient note one or more symptoms that the patient was experiencing, the results of a physical examination that the caregiver performed, an assessment the patient's condition, a plan for treatment of the symptoms, as well as other possible information. After the patient note is completed, the patient note is stored in the patient's medical record, where it can be reviewed by the caregiver during subsequent interactions.

SUMMARY

In general terms, this disclosure is directed to a caregiver interface for electronic medical records. In one possible configuration and by non-limiting example, the caregiver interface displays a patient note including at least one finding. When the finding is selected by the caregiver, the caregiver interface is updated to identify historical data relating to the selected finding.

One aspect is a method of generating a user interface, the method comprising: receiving an input, the input identifying a physical characteristic of a patient; in response to receiving an input, generating a data item identifying the physical characteristic of the patient; storing the data item in a first note data record of a data storage device; displaying a user interface having a first note data display, the first note data display displaying data items from the first note data record; and generating a second note data display displaying data items from a second note data record, the second note data record also containing the data item.

Another aspect is a method of generating a user interface, the method comprising: receiving an input of a data item; displaying the data item in a user interface with a selectable control; and upon actuation of the selectable control, displaying one or more additional selectable controls, each additional selectable control being associated with a historical note data record that includes the data item.

Yet another aspect is a method of generating a user interface, the method comprising: displaying a first note data record containing a data item representing a physical characteristic of a patient, the data item being displayed in a first font; and assigning a color to the font, wherein the color is indicative of the physical characteristic.

A further aspect is a method of generating a user interface, the method comprising: displaying a user interface having a first note data record in a first frame, the first note data record including a data item; receiving an input identifying the data item of the first note data record, the data item representing a physical characteristic of a patient; upon determining whether the data item is included in a second note data record, generating a selectable control linked to the second note data record; and displaying the selectable control in the first frame while the first note data record is being displayed in the first frame.

Another aspect is a method of generating a user interface, the method comprising: generating a user interface having a first note data display corresponding to an encounter with a patient, the first note data display displaying a data item identifying the physical characteristic of the patient; and displaying the data item with a color in the user interface, the color identifying a state of the physical characteristic of the patient.

Another aspect is an apparatus comprising a display device, memory storing one or more historical note data records, and a processor in data communication with the display device and memory. Each historical note data record includes at least one data item. The processor is programmed to identify a data item, identify a historical data record associated with the data item; and generate a user interface including the data item and a selectable control associated with the data item in the user interface, the selectable control comprising a link to the historical note data record.

Another aspect is an apparatus comprising a display device, memory storing one or more historical note data records, and a processor in data communication with the display device and memory. Each historical note data record includes at least one data item. The processor is programmed to generate a user interface comprising a first window displaying a first note data record, the first note data record displaying a first set of data associated with a first patient encounter, the first set of data including a first note data item; a second window displaying a second note data record, the second note data record displaying a second set of data associated with a second patient encounter. The second set of data comprises the same first note data item as the first window and a selectable control visible in the user interface when at least the first window is displayed. The selectable control is operable to bring the second window to a front of the user interface when selected.

Another aspect is an apparatus comprising a display device, memory storing one or more historical note data records, and a processor in data communication with the display device and memory. Each historical note data record includes at least one data item. The processor is programmed to generate a user interface comprising a first window displaying a first note data record, the first note data record displaying a first set of data associated with a first patient encounter, the first set of data including a first note data item; and a selectable control associated with the first note data item. Upon selection of the selectable control, the user interface is updated to display additional selectable controls associated with historical records including the same first note data item.

Another aspect is an apparatus comprising a display device, memory storing one or more historical note data records, and a processor in data communication with the display device and memory. Each historical note data record includes at least one data item. The processor is programmed to generate a user interface comprising a first window displaying a first note data record, the first note data record displaying a first set of data associated with a first patient encounter, the first set of data including a first note data item associated with a characteristic of the patient. The first note data item has a value associated with a state, the value representing a state of a physical characteristic of a patient. The first note data item is displayed in a color identifying the state.

BRIEF DESCRIPTION OF THE DRAWINGS

FIG. 18 is another screen shot of the example caregiver user interface shown in FIG. 15.

DETAILED DESCRIPTION

Figure 1:
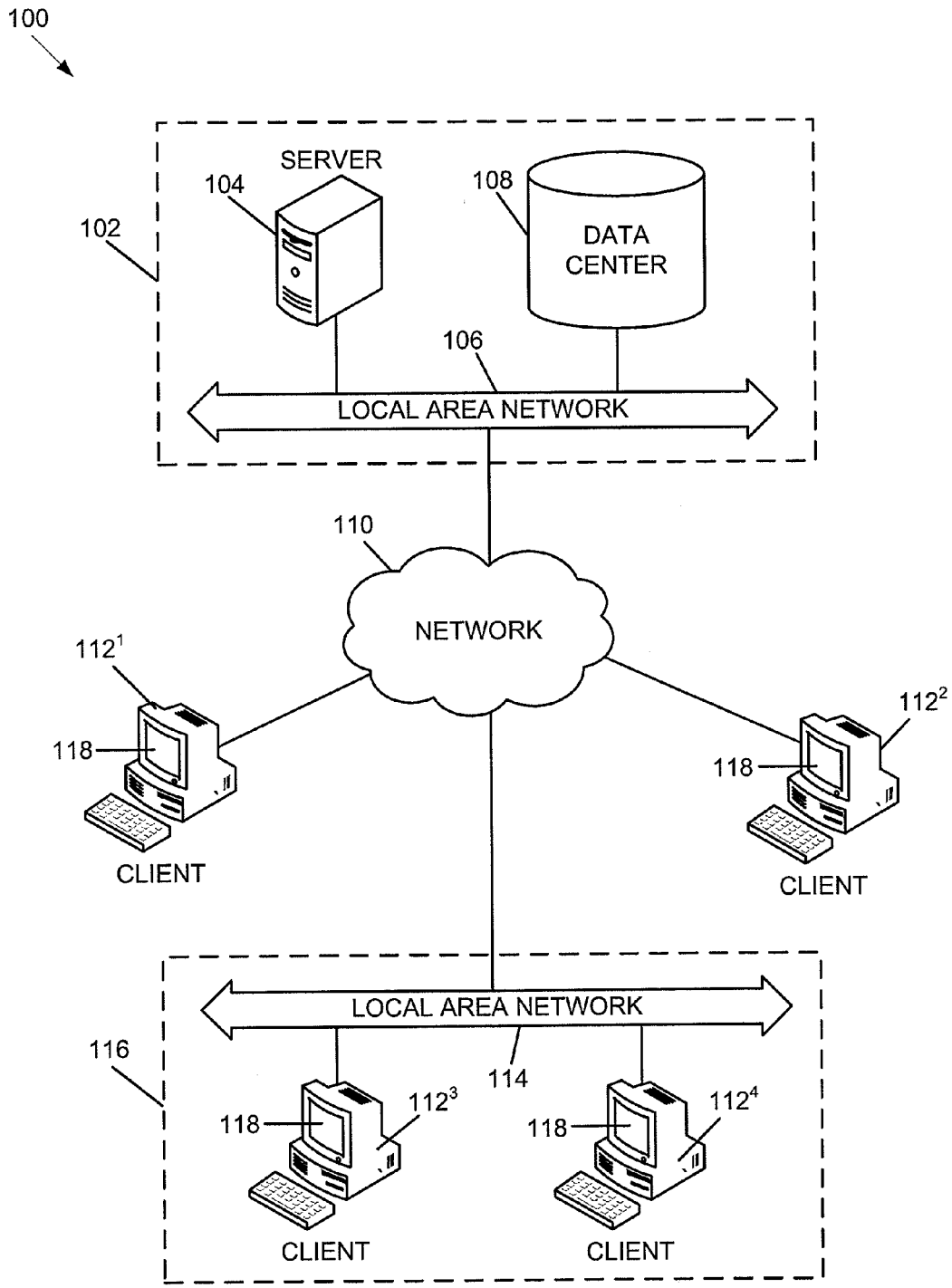
FIG. 1 is a schematic diagram illustrating an exemplary electronic medical records system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 illustrates an exemplary embodiment of an electronic medical records system 100. The system 100 includes a healthcare information management system 102, a network 110, and clients 112. Clients 112 include stand-alone clients $112^1$ and $112^2$ as well as networked clients $112^3$ and $112^4$ that are connected to local area network 114.

Some embodiments of healthcare information management system 102 include a server 104 and a data center 108 that communicate across local area network 106. The healthcare information management system 102 operates to store medical records of patients and to send selected portions of the medical records across network 110 when requested by a client 112. The healthcare information management system 102 can be located at the same location (such as in the same room, building, or facility) as one or more of the clients 112. Alternatively, the healthcare information management system 102 is located remote from the clients 112, such as in a different building, city, state, country, or continent.

The server 104 controls access to records stored in the healthcare information management system 102, in some embodiments. In one example embodiment, the server 104 is a computing device that includes a database software application, such as the SQL SERVER® database software distributed by MICROSOFT® Corporation. In some other possible embodiments, the server 104 is a Web server or a file server. When a request for a record is received by the server 104, the server retrieves the record from the data center 108 and sends it across the network 110 to the client 112 that requested it. Some alternative embodiments do not include a server 104, and, instead, clients 112 are configured to retrieve information directly from the data center 108.

The data center 108 is a data storage device configured to store patient medical records. Examples of a possible data center 108 include a hard disk drive, a collection of hard disk drives, digital memory (such as random access memory), a redundant array of independent disks (RAID), or other data storage devices. In some embodiments records are distributed across multiple local or remote data storage devices. The data center 108 stores data in an organized manner, such as in a hierarchical or relational database structure. Although the data center 108 is illustrated as being separated from the clients 112 by the network 110, the data center 108 is alternatively a local data storage device of a client 112 or is connected to the same local area network 114 as the client 112.

The network 110 communicates digital data between one or more computing devices, such as between the healthcare information management system 102 and the clients 112. Examples of the network 110 include a local area network and a wide area network, such as the Internet.

In some embodiments, the network 110 includes a wireless communication system, a wired communication system, or a combination of wireless and wired communication systems. A wired communication system can transmit data using electrical or optical signals in various possible embodiments.

In some example embodiments, clients 112 are computing devices used by a caregiver that generate a caregiver interface 118. Caregivers include physicians, psychiatrists, counselors, therapists, medical assistants, secretaries, receptionists, or other people that are involved in providing care to a patient. Other embodiments present the user interface to users that are not caregivers. In some embodiments, a client 112 is located at a point of care, such as within a room where a caregiver and a patient interact. In other embodiments, a client 112 is located near the point of care, such as in a hallway or nearby room. However, in other possible embodiments the client 112 is not located near the point of care.

In one example embodiment, the electronic medical records system 100 includes stand-alone clients $112^1$ and $112^2$, as well as networked clients $112^3$ and $112^4$. Stand-alone clients $112^1$ and $112^2$ connect directly to network 110 and are not part of an additional local area network. Networked clients 112³ and 112⁴ are connected to a local area network 114 which may be within a facility 116, such as a hospital, clinic, office, or other building. More or fewer clients 112 are included in other possible embodiments and can be located in one or more facilities or locations.

Figure 2:
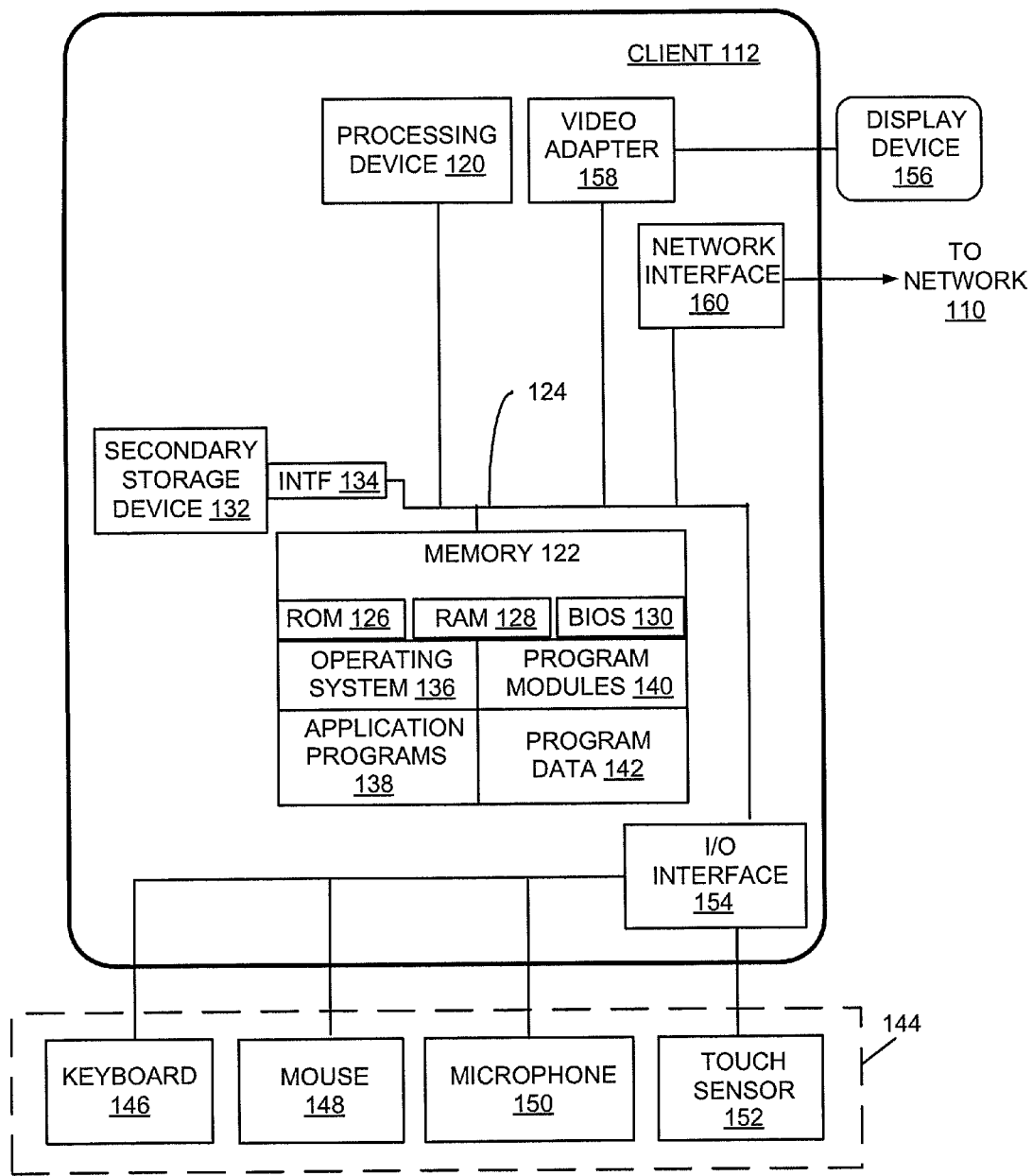
FIG. 2 is a schematic block diagram illustrating an exemplary architecture of a computing device for implementing aspects of the electronic medical records system shown in FIG. 1.

FIG. 2 illustrates an exemplary architecture of a computing device that can be used to implement aspects of the present disclosure, including the server 104 or the client 112, and will be referred to herein as the client 112. The client 112 is used to execute the operating system, application programs, and software modules (including the software engines) described herein.

The client 112 includes, in some embodiments, at least one processing device 120, such as a central processing unit (CPU). A variety of processing devices are available from a variety of manufacturers, for example, Intel or Advanced Micro Devices. In this example, the client 112 also includes a system memory 122, and a system bus 124 that couples various system components including the system memory 122 to the processing device 120. The system bus 124 is one of any number of types of bus structures including a memory bus, or memory controller; a peripheral bus; and a local bus using any of a variety of bus architectures.

Examples of computing devices suitable for the client 112 include a desktop computer, a laptop computer, a tablet computer, a mobile device (such as a smart phone, an iPod® mobile digital device, or other mobile devices), or other devices configured to process digital instructions.

The system memory 122 includes read only memory 126 and random access memory 128. A basic input/output system 130 containing the basic routines that act to transfer information within client 112, such as during start up, is typically stored in the read only memory 126.

The client 112 also includes a secondary storage device 132 in some embodiments, such as a hard disk drive, for storing digital data. The secondary storage device 132 is connected to the system bus 124 by a secondary storage interface 134. The secondary storage devices and their associated computer readable media provide nonvolatile storage of computer readable instructions (including application programs and program modules), data structures, and other data for the client 112.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 132 or memory 122, including an operating system 136, one or more application programs 138, other program modules 140, and program data 142.

In some embodiments, a caregiver provides inputs to the client 112 through one or more input devices 144. Examples of input devices 144 include a keyboard 146, mouse 148, microphone 150, and touch sensor 152 (such as a touchpad or touch sensitive display). Other embodiments include other input devices 144. The input devices are often connected to the processing device 120 through an input/output interface 154 that is coupled to the system bus 124. These input devices 144 can be connected by any number of input/output interfaces, such as a parallel port, serial port, game port, or a universal serial bus. Wireless communication between input devices and interface 154 is possible as well, and includes infrared, BLUETOOTH® wireless technology, 802.11a/b/g/n, cellular, or other radio frequency communication systems in some possible embodiments.

In this example embodiment, a display device 156, such as a monitor, liquid crystal display device, projector, or touch screen display device, is also connected to the system bus 124 via an interface, such as a video adapter 158. In addition to the display device 156, the client 112 can include various other peripheral devices (not shown), such as speakers or a printer.

When used in a local area networking environment or a wide area networking environment (such as the Internet), the client 112 is typically connected to the network through a network interface, such as an Ethernet interface 160. Other possible embodiments use other communication devices. For example, some embodiments of the client 112 include a modem for communicating across the network.

The client 112 typically includes at least some form of computer-readable media. Computer readable media includes any available media that can be accessed by the client 112. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the client 112.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Figure 3:
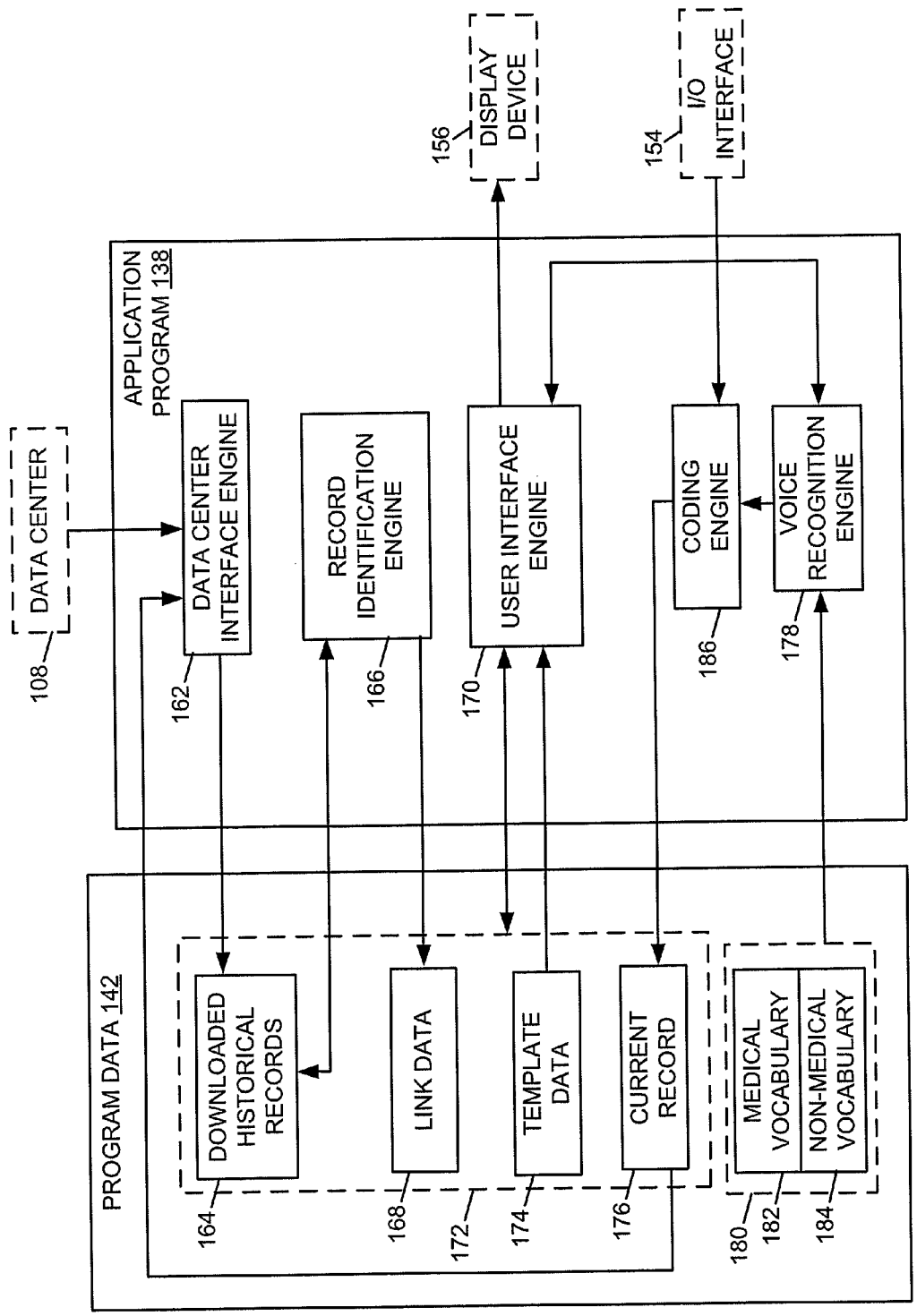
FIG. 3 is a schematic block diagram illustrating an exemplary architecture of an application program.

FIG. 3 illustrates an exemplary architecture of the application program 138 and the program data 142 of the client 112 (shown in FIG. 2). Application program 138 includes a plurality of modules that, when executed by the processor, perform one or more operations of the application program 138. The modules include a data center interface engine 162, a record identification engine 166, a user interface engine 170, a voice recognition engine 178, and a coding engine 186.

Program data 142 is stored in a data storage device, such as the memory 122 or the secondary storage device 132 (shown in FIG. 2). In some embodiments, program data 142 includes user interface data 172 and a word base 180. The user interface data 172 includes data used to generate user interfaces or that is displayed in user interfaces. Examples of user interface data 172 includes downloaded historical records 164, link data 168, template data 174, and current record 176. The word base 180 includes, for example, medical vocabulary 182 and non-medical vocabulary 184.

In an exemplary embodiment, the data stored in program data 142 can be represented in one or more files having any format usable by a computer. Examples include text files formatted according to a markup language and having data items and tags to instruct computer programs and processes how to use and present the data item. Examples of such formats include html, xml, and xhtml, although other formats for text files can be used. Additionally, the data can be represented using formats other than those conforming to a markup language.

In some embodiments disclosed herein, findings are stored as data items in one or more data records. In some embodiments, data records are a set of one or more data items, such as in a format that can be read by a computing device. An example embodiment is a database record. Other examples of data records include tables, text files, computer executable files, data structures, or other structures for associating data items.

In some embodiments, application program 138 communicates with the data center 108 of the healthcare information management system 102, and also communicates with the display device 156 and the input/output interface 154 of the client 112. Such communication between the application program 138 and healthcare information management system 102 can occur through the server 104. In some possible embodiments the application program 138 resides on client 112, while in other possible embodiments application program 138 resides on a server. As one example, if the application program 138 resides on the server, the caregiver interface 118 can be presented as a web page file that is communicated to the client 112. In this example, the client 112 receives the web page file from the server and generates the caregiver user interface 118 using a Web browser software application.

Figure 4:
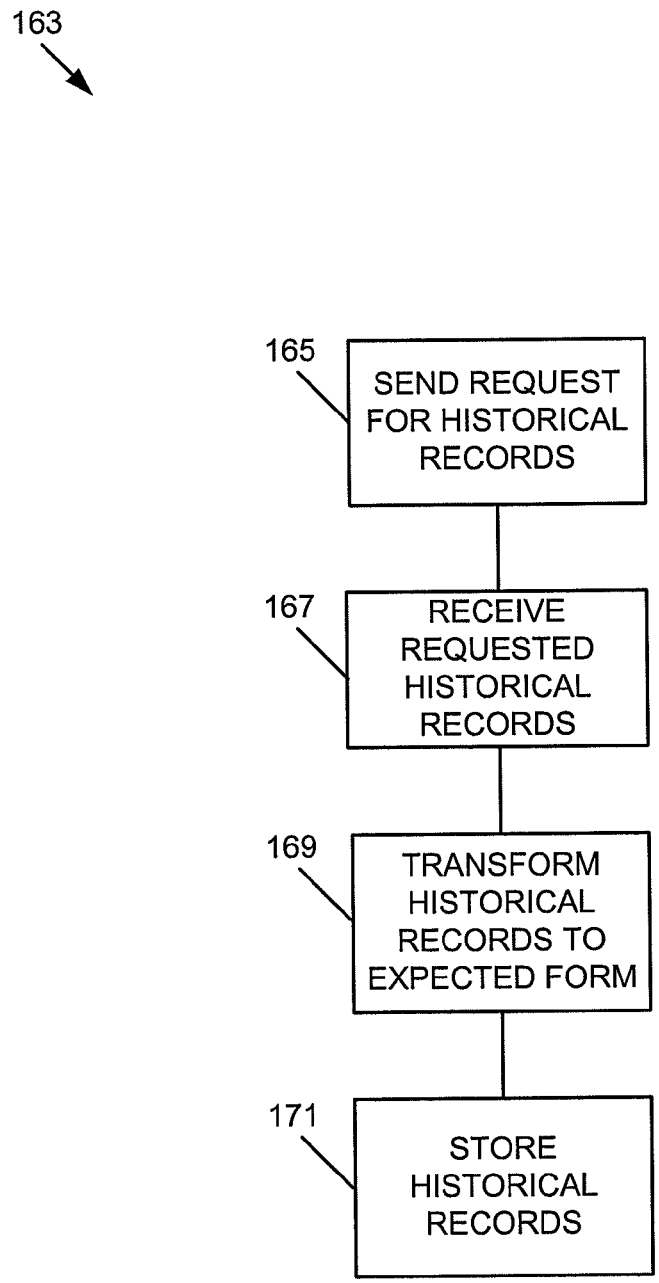
FIG. 4 is a schematic flow chart illustrating an exemplary method of operating a data center interface engine.

The data center interface engine 162 operates to download historical records from the data center 108. Referring now to FIG. 4, an exemplary method 163 of operating a data center interface engine 162 is illustrated. In some embodiments, the method includes operations 165, 167, 169, and 171 that are performed by a processor (such as the processing device 120, shown in FIG. 2). As used herein, methods include actions or processes that are performed by a user or executed by a computer, or combinations of these.

In this example, the method 163 begins with an operation 165, in which the data center interface engine 162 of the client 112 sends a request for historical records to the healthcare information management system 102. The request identifies the records that are needed from the data center 108. The identification of the records can be either an identification of specific records, or an identification of a search query to be performed across the records stored in the data center 108. In some embodiments, the operation 165 involves sending a request to the server 104, which receives the request, locates the records identified in the request, and sends the records back to the data center interface engine 162. The operation 167 is then performed to receive the records.

After the records are downloaded, the operation 169 is then performed to transform the historical records from a first format (the format the records are in when retrieved from the data center 108) into a second format (the format that the application program 138 needs the historical records to be in). A wide variety of formats can be used to store patient medical records in the data center 108. For example, in one possible embodiment, the first format of the historical records is an SQL database format. In another possible embodiment, the first format is an extensible markup language format. Other relational database formats are used in other embodiments.

Yet other embodiments use other data structures to store historical records in the data center 108.

The application program 138 is configured to use the historical data in a second format, which can be different from the first format. An example of the second format is an extensible markup language format utilizing linked lists, and/or hash tables to organize and relate the data. As a result, the operation 169 transforms the historical records from the first format into the second format.

Once the historical records have been transformed to the desired format, they are stored during the operation 171 as downloaded historical records in the program data 142 (shown in FIG. 3). In some embodiments, however, the historical records received in the operation 167 are usable by the application program 138 in their received form. In this case, the operation 169 does not need to be performed, and the operation 171 is instead performed following the operation 167 to store the downloaded historical records in the program data 142.

Returning now to FIG. 3, some embodiments of the application program 138 are configured to accept one of a variety of data center interface engines 162 as plug-in modules. The plug-in modules allow the application program 138 to be compatible with various data center 108 formats without requiring custom programming of the application program 138 for every possible format of records in the data center 108.

In some embodiments that utilize a plug-in module structure for the data center interface engine 162, when the application program 138 is installed on the client 112, a plug-in module is selected from a plurality of plug-in modules. The selected plug-in module is configured to communicate with and receive historical records in a format that matches the first format of records in the data center 108, and to transform the historical records into the second format expected by the application program 138.

Figure 5:
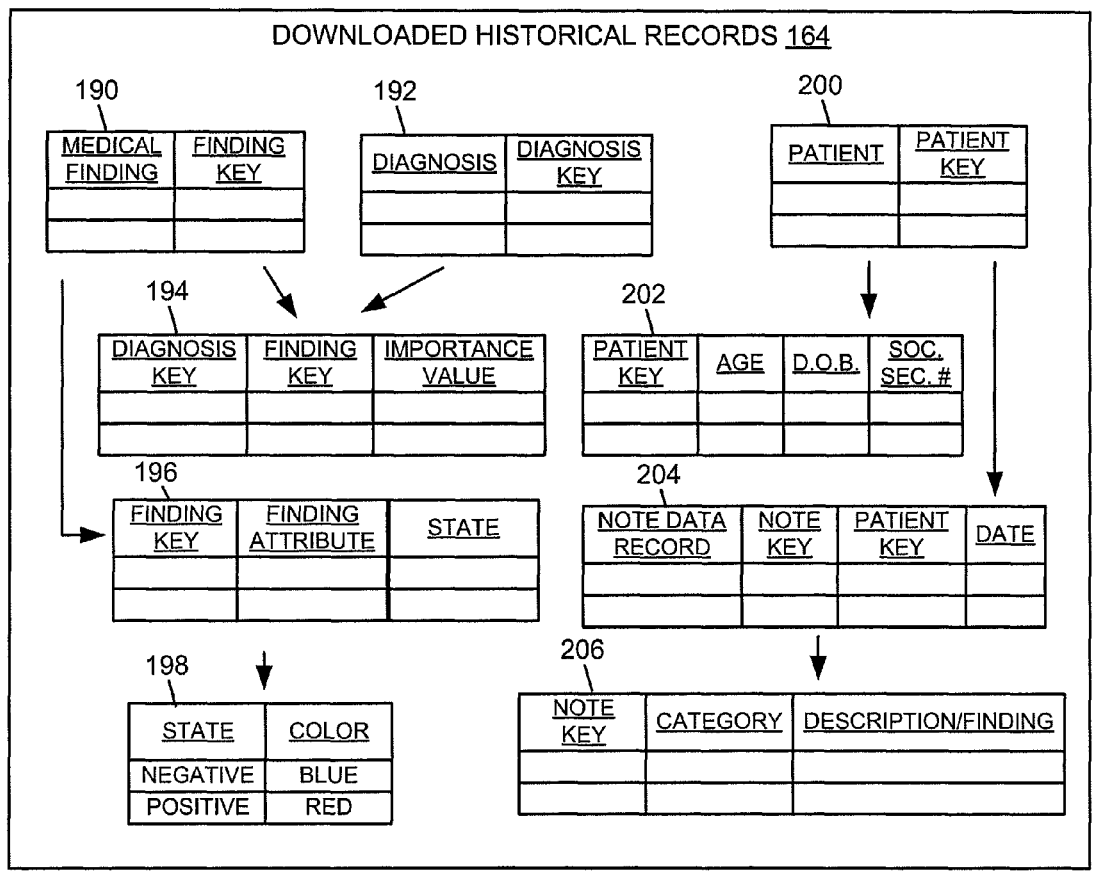
FIG. 5 is a schematic block diagram illustrating an exemplary format of downloaded historical records.

Referring now to FIG. 5, an example format of downloaded historical records 164 is illustrated. In this example, downloaded historical records are contained in a plurality of data structures in the form of tables utilizing data keys. Other embodiments include other types of data structures and other methods of linking data structures.

In one example embodiment, the downloaded historical records 164 include a medical findings table 190, a diagnosis table 192, a findings importance table 194, a state table 196, a color table 198, a patient table 200, a patient data table 202, a note data record table 204, and a note details table 206. Additional tables are included in other embodiments as needed. Further, some embodiments include different table structures, such as to merge data from multiple tables into a single table or to separate data from a single table into multiple tables.

The medical findings table 190 includes a list of the available medical findings, and maps each medical finding to a unique finding key. Medical findings identify physical characteristics of a person, such as the patient. In some embodiments, medical findings include symptoms (also referred to herein as chief complaints) that a patient is experiencing, relevant medical history of the patient or patient's family, findings from a physical examination of the patient, diagnoses of the patient, tests performed on a patient and the results of the tests, and therapy performed or prescribed. Each finding is mapped to a unique finding key, which can be used to refer to the medical finding in other data structures. Some embodiments, for example, include a medical findings table 190 having more than 200,000 possible medical findings.

In some embodiments, the medical findings are organized in a hierarchical structure that provides various levels of abstraction for medical findings. As one example, a hierarchical structure can include multiple levels, where findings in the first level are generic descriptions of medical findings, and findings in the lower levels include more detailed descriptions of those medical findings. For example, a first level medical finding might be a cough, while a second level medical finding associated with the cough might be a brassy cough. Additional data structures are provided in some embodiments to link medical findings to the various levels in a hierarchical structure. Some embodiments further associate each finding with a category, such as by including a category column (not shown) in the medical finding table 190. Examples of findings categories include a symptom, a medical history, a physical examination finding, a diagnosis, a test, and a therapy. Other embodiments include more or fewer categories.

The diagnosis table 192 includes a list of the available diagnoses, and maps each diagnosis to a unique diagnosis key. The diagnoses are then mapped to the findings using the findings importance table 194.

The findings importance table 194 associates each diagnosis of diagnosis table 192 with the relevant medical findings, and also identifies the relative importance of the medical finding to the diagnosis. The relative importance of each finding is assigned a number, such as a number in a range from 1 to 20. A low number means that that respective finding has relatively lower importance than a high number which has relatively higher importance to that finding. Other embodiments include other ranges of importance values.

The state table 196 associates findings with a state of that finding. In this example, the state table 196 identifies a finding with the finding key (from the medical finding table 190) and identifies an attribute of that finding. The finding and finding attribute are then associated with a state. In this example, the state is selected from a first state, such as positive, and a second state, such as negative. A negative state indicates that the finding and attribute are within a normal range, while a positive finding indicates that the finding and attribute are within an abnormal range. Other embodiments include other states, such as normal and abnormal. Yet other embodiments include more than two possible states. Attributes are sometimes alternatively referred to as values herein.

The color table 198 associates each available state with a color to identify the state in the caregiver interface. In this example, a negative state is associated with a first color (blue) and a positive state is associated with a second color (red). More or fewer states and colors are used in other embodiments. Further, other embodiments utilize formatting other than color, such as a style (regular, italics, bold, underline, double underline, etc.), or other visual indicators (graphical images or symbols, such as a red flag or plus sign as an identifier of an abnormal finding and a green circle or a minus sign as an indication of a normal finding, etc.).

The patient table 200 includes a list of one or more patients and maps each patient to a patient key. The patient data table 202 stores additional information about one or more patients. The patient data table 202 identifies the patient using the patient key from patient table 200, and further includes additional information about the patient. In one possible example, the additional information includes the patient's age, date of birth, and social security number. Other embodiments include more or less patient information.

The note data record table 204 includes a list of note data records. When a physician interacts with a patient, a summary of the caregiver's findings are stored in a note data record. The note data record table 204 includes a list of the note data records and maps each note data record to a note key. In this example, the note data record table 204 also maps the note data record to a patient using the patient key from the patient table 200 and includes the date that the record was generated.

The note details table 206 contains the summary of the findings for each note data record. In one example embodiment, the note details table 206 associates note data records with a category and a description or finding. For example, if a patient was complaining of having a cough, the note data record can be associated with a category of "symptom" and include a description or finding of "cough." In some embodiments the descriptions are string data fields that store any data entered by the caregiver. In other embodiments the description is limited to specific findings selected from the medical finding table 190.

This example structure of the downloaded historical records 164 illustrated in FIG. 4 is an example of one possible structure. Various other embodiments utilize other data structures and contain more or less data fields as desired.

Although the downloaded historical records 164 are described as residing on the client 112, other possible embodiments store the historical records in other locations. For example, in some embodiments the historical records are stored on the server 104 or in the data center 108, rather than in the client 112. One such alternative embodiment provides the caregiver interface 118 through a client's Web browser software application, such as to provide the caregiver interface 118 as a service (e.g., Software as a Service). In this example, the server 104 performs many of the operations described herein instead of the client 112. Alternatively, in another possible embodiment the client 112 stores the downloaded historical records 164 in another database, such as on another computing device.

Returning now to FIG. 3, some example embodiments of the application program 138 include a record identification engine 166. The record identification engine 166 operates to identify the relationships between historical records. More specifically, the record identification engine 166 identifies historical records that contain a common data item, and then stores the relationships between the historical records and the data item as link data 168 in the program data 142.

In some embodiments, the record identification engine 166 includes at least two modes of operation. The first mode is a template initiation mode that begins when a template is selected by the caregiver. The second mode is an update mode that updates the links between records as new information is obtained from a caregiver as discussed in more detail below.

Figure 6:
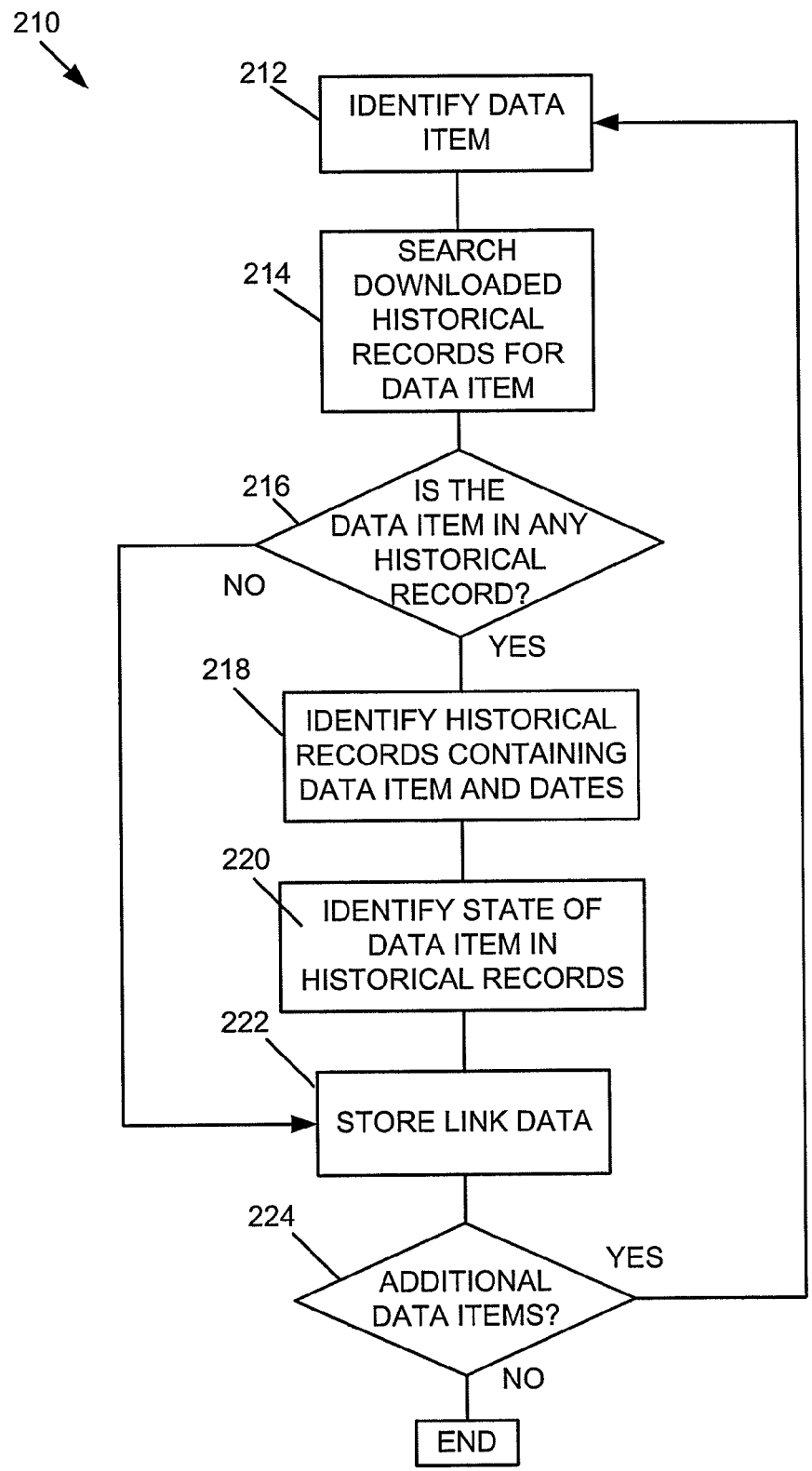
FIG. 6 is a schematic flow chart illustrating an exemplary method of operating a record identification engine.

An exemplary method 210 of operating the record identification engine 166 is illustrated in FIG. 6. In some embodiments, the method 210 is executed by the processing device 120 to perform operations 212, 214, 216, 218, 220, 222, and 224.

The example method 210 begins with an operation 212 to identify a data item. In some embodiments the data item is a medical finding that identifies a physical or mental characteristic of a person, such as the patient or a relative of the patient. When operating in the template initiation mode, the method 210 operates to search a patient's historical records to determine if any of the data items identified in one or more templates selected from the template data 174 are contained in any of the patient's historical records. Accordingly, the operation 212 begins by identifying the first data item in the selected template. After the first data item has been processed (operations 214, 216, 218, 220 and 222), operations 224 and 212 are performed to identify the next data item. The method 210 continues to process each data item until all data items of the patient's medical record have been processed. In some embodiments, the method 210 is repeated each time a template is selected.

When operating in the update mode, the operation 212 is performed each time that a data item is entered by a caregiver. Upon entry of a data item, the method 210 then processes the new data item to identify historical records that contain that same data item.

Once a data item has been identified, an operation 214 is next performed to search the downloaded historical records 164 for the data item.

An operation 216 then determines whether the data item is found in any of the historical records and, if not, the method 210 advances to an operation 222. If at least one historical record is found that contains the data item, then an operation 218 is performed to identify the historical records that contain the data item. For example, the note key associated with each of the historical records is identified from the note data record 204. In some embodiments, the date of each historical record is also identified. Other identifiers or information relating to the historical records are identified in yet other embodiments.

An operation 220 is also performed to identify the state of the data item in each historical record. In one example, an operation 220 locates the attributes associated with the data item from the historical record, and utilizes the state table 196 to determine a state associated with the data item and attribute.

An operation 222 is then performed to generate and store link data to associate the data item with the identified historical records. In one example, an operation 222 generates one or more data records that include an identification of the data item, an identification of each historical record that contains the data item, an identification of the date of each historical record that contains the data item, and an identification of the state of the data item in each historical record. In this way the data item is associated with each historical record that contains the data item. The data records are then stored as link data 168. Other embodiments identify and store more or less information about the historical records, as desired.

After the link data 168 has been stored, an operation 224 is performed to determine whether there are additional data items to be processed. If so, the method 210 returns to the operation 212 to identify the next data item. If there are no further data items to be processed, the method 210 ends.

Some alternative embodiments of the method 210 include more or fewer operations. Further, some embodiments perform the operations in a different order than illustrated in FIG. 6.

Returning now to FIG. 3, some embodiments of the application program 138 include the user interface engine 170 that generates the caregiver interface 118 on the display device 156.

The user interface engine 170 utilizes the user interface data 172 of the program data 142 to generate the caregiver interface. In this example, the user interface data 172 includes the downloaded historical records 164, the link data 168, the template data 174, and the current record 176 that are stored in the program data 142. The template data 174 stores a variety of different templates that can be used by the user interface engine 170 to generate a current note data display, as discussed in more detail herein. The templates are used by the user interface engine 170, for example, to organize findings entered by a caregiver and to suggest additional findings that may be relevant to the patient's condition.

The user interface engine 170 receives inputs from a caregiver through the input/output interface 154. Examples of such inputs include inputs from a keyboard 146, a mouse 148, or a touch sensor 152. In some embodiments, voice inputs are received from a caregiver through a microphone 150. The voice inputs are processed by a voice recognition engine 178, discussed in more detail below, and then provided as an input to the user interface engine 170.

Figure 7:
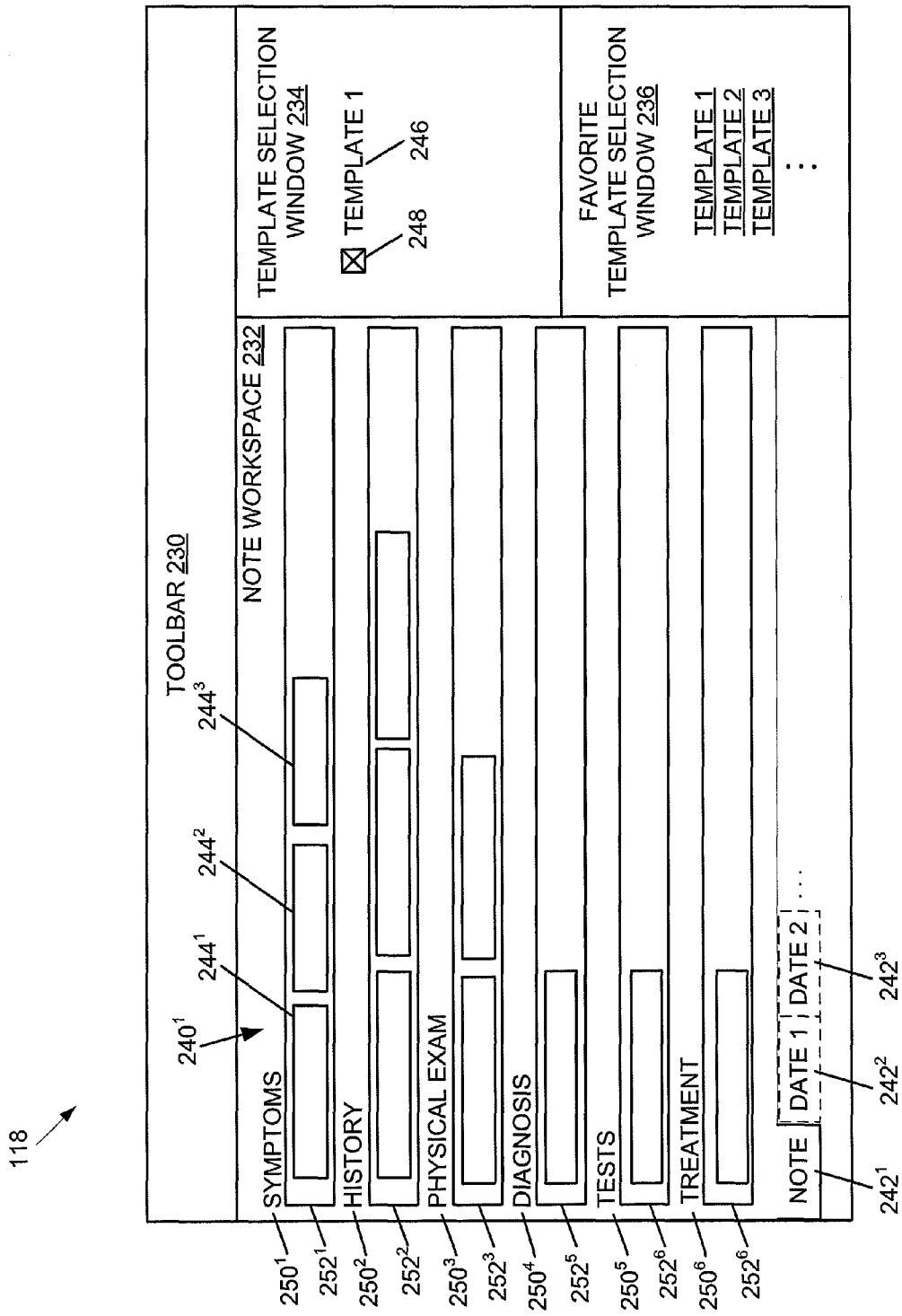
FIG. 7 is a schematic block diagram illustrating an exemplary layout of a caregiver interface.

Referring now to FIG. 7, a block diagram illustrating an example layout of the caregiver interface 118 is shown as generated by the user interface engine 170. The caregiver interface 118 includes a toolbar 230, a note workspace 232, a template selection window 234, and a favorite template selection window 236. The note workspace 232 includes one or more note data displays 240 and a selectable control 242 associated with each note data display 240.

The toolbar 230 provides a set of tools (not shown in FIG. 7) that are selectable by the caregiver to initiate an associated function. In this example, the toolbar 230 is arranged along a top of the caregiver interface 118. In an example embodiment, the toolbar 230 includes tools, such as file management tools, template management tools, patient selection tools, formatting tools, dictation tools, and administrative tools. Other embodiments include more or fewer tools. Some embodiments do not include the toolbar 230, or include the other selectable controls suitable for initiating associated functions. In some embodiments, the toolbar is located in a different part of the caregiver interface 118, and can be arranged in a separate or expandable window, if desired.

In an example embodiment, the note workspace 232 is a window that presents one or more note data displays 240 to the caregiver. Note data displays 240 include a current note data display (where the caregiver can record findings of a current interaction or encounter) and can also include one or more historical note data displays (where the caregiver can review findings from prior interactions or encounters). The current note data display $240^1$ operates to display findings stored in the current record 176 (shown in FIG. 3) as well as to display new findings when entered by the caregiver. As new findings are entered by the caregiver, the new findings are also stored in the current record 176. Historical note data displays (such as $240^2$ and $240^3$, which are not visible in FIG. 7) are each associated with a downloaded historical record 164 (shown in FIG. 3) and display the findings from a prior interaction or encounter between the caregiver (or another caregiver) and the patient.

Each note data display 240 is linked to a selectable control 242. When the control 242 is selected by the caregiver, the user interface engine 170 updates the caregiver interface 118 to display the note data display 240 in the workspace 232 that is linked to the selected control 242. In this example, control the $242^1$ (labeled "NOTE" in FIG. 7) is a current control that is linked to the current note data display $240^1$. Controls $242^2$ and $242^3$ are historical controls that are linked to historical note data displays $240^2$ and $240^3$, respectively (not visible in FIG. 7). One example of the selectable control 242 is a tab, as shown in FIG. 7. Other embodiments include other selectable controls, such as a button, link, icon, dropdown menu, selectable list, check box, etc.

In some embodiments, when a new patient interaction begins, the caregiver interface 118 is generated, and includes a blank current note data display $240^1$. To begin making a record of the interaction, the caregiver can select one or more templates from template selection window 234 or favorite template selection window 236.

Some embodiments include a favorite template selection window 236 that displays a list of the caregiver's most frequently used, or "favorite," templates. When a template is selected by the caregiver, the user interface engine 170 reads the associated template from template data 174 stored in program data 142 (shown in FIG. 3) and displays the template in the current note data display 240$^1$. An example template is shown in FIG. 7. In some embodiments, templates include a layout that defines the organization and visual arrangement of data, a plurality of finding categories 250, and associated input fields 252 where findings from the current interaction can be recorded in the current note data display 240$^1$. In some embodiments, the templates also include a plurality of data items 244, which are suggested data items that are likely to be relevant to the current interaction. If the caregiver enters a finding associated with the suggested data item, the data item 244 is displayed in current note data display 240$^1$ and the associated data is saved in the current record 176. In some embodiments each template is associated with a particular type of interaction, such as a routine examination, a follow up visit for a particular condition, an intake examination, or a variety of other possible types of interactions. In some embodiments, templates also contain suggested findings to help guide the caregiver during the interaction.

Some embodiments further include a template selection window 234. When a template is added to the current note data display 240$^1$, the name 246 of the template is displayed in the template selection window 234 along with a selectable control 248, such as a check box. The selectable control 248 is selectable by the caregiver to toggle the display of the template in the current note data display 240$^1$. For example, if the caregiver selects the selectable control 248 to deselect the check box, current note data display 240$^1$ is updated to remove the template associated with template 1. If multiple templates are selected at the same time in the template selection window 234, the templates are merged and displayed as a single combined template in current note data display 240$^1$.

Figure 8:
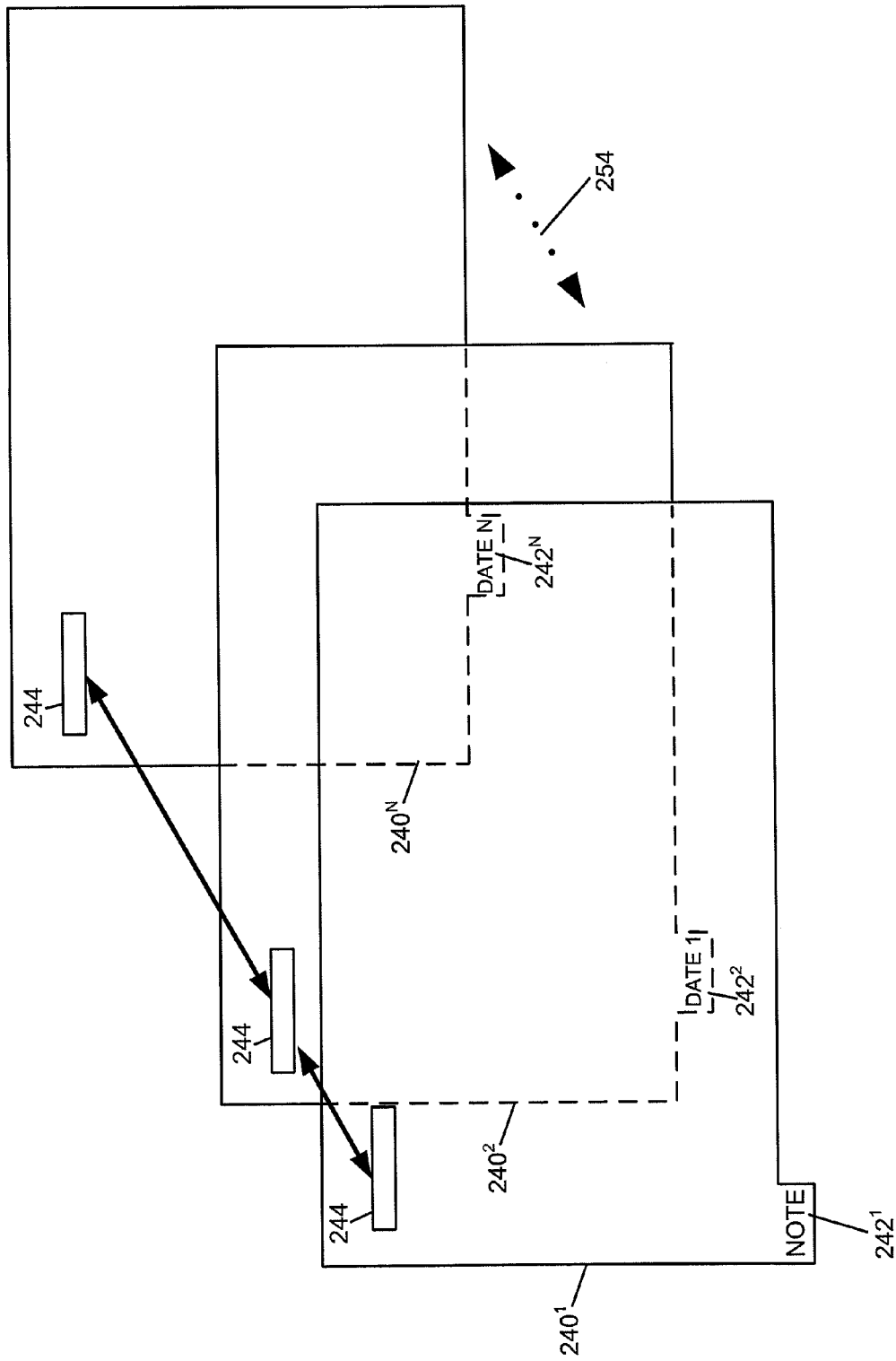
FIG. 8 is a schematic diagram illustrating the linking of data items with historical note data displays.

Referring now to FIG. 8, a schematic diagram illustrates the linking of data items with historical note data displays 240$^2$ and 240$^N$ by user interface engine 170. Note data displays 240 are selectively displayed in caregiver interface 118, such as shown in FIG. 7, but one graphically depicted in FIG. 8 as being offset from each other so that details of each of the note data displays 240$^1$, 240$^2$, 240$^N$ are visible for the following discussion.

This example includes a current note data display 240$^1$ and two historical note data displays 240$^2$ and 240$^N$. As illustrated by an ellipse 254, any number of historical note data displays 240$^2$ and 240$^N$, can be included in various embodiments. Each note data display 240 includes an associated control 242 and an associated data item 244.

The user interface engine 170 operates, in some embodiments, to display relationships between data items 244 and note data records (as displayed by note data displays 240). For example, when the caregiver interface 118 is displaying the current note data record 240$^1$, data item 244 is displayed. The data item 244 can be either a suggested data item provided by a template, or an entered data item provided by a caregiver based on the current interaction. In some embodiments data items include a finding and a value of the finding.

When the current note data display 240$^1$ is displayed in the caregiver interface 118, the data items, such as the data item 244, are also displayed. In some embodiments, the user interface engine 170 checks the link data 168 of the program data 142 (shown in FIG. 3) to determine whether the data item 244 has been found in any of the downloaded historical records 164 associated with the current patient. If any historical records 164 contain the same data item 244, then the display of that data item 244 is formatted in a different format, such as by underlining the data item 244 in the current note data display 240$^1$. Other embodiments include other formatting, such as bold, italics, double underline, a font color or pattern, a background color or pattern, or any other formatting that visually distinguishes the data item 244 from data items that do not have any historical data records. When the data item 244 is selected, the caregiver interface 118 operates to determine whether there are any historical records for the current patient that include the same data item 244. The determination is made, for example, by checking link data 168 to see if the data item 244 is associated with any historical records. If so, the caregiver interface 118 is updated to display information about the historical records. In this example, the user interface engine 170 determines that the data item 244 is associated with two historical records, and generates historical note data displays 240$^2$ and 240$^N$ for each historical record. As shown, each historical note data display includes the same data item 244 as the data item selected in current note data display 240$^1$. If desired, the caregiver can select one of the controls 242$^2$ or 242$^N$ to cause caregiver interface 118 to display the historical note data display 240$^2$ and 240$^N$ linked to that control.

In some embodiments, a data item is considered the same as another data item if they share a common finding, regardless of the value of the finding.

Figure 9:
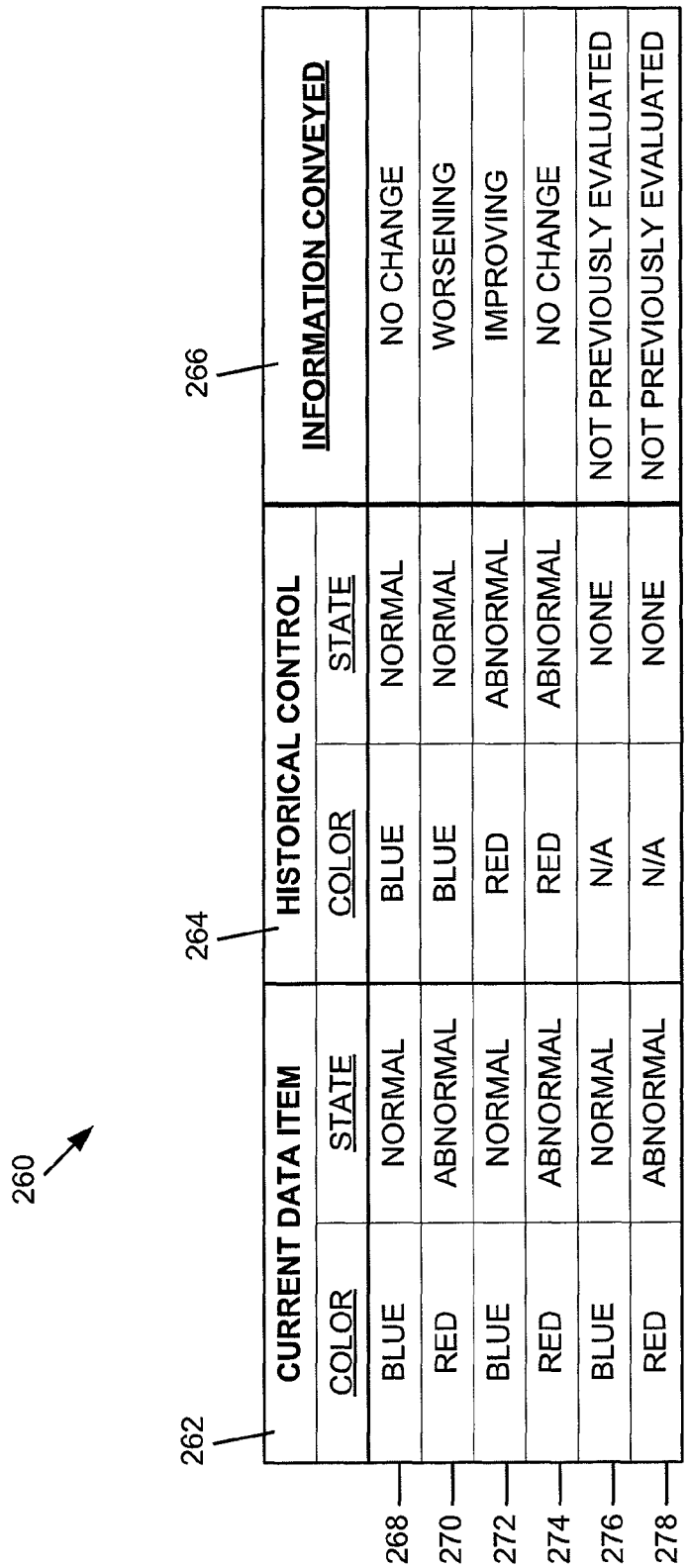
FIG. 9 is a table illustrating an example of colors that can be displayed in a caregiver interface to convey information to the caregiver.

FIG. 9 is a table 260 illustrating an example of colors that can be displayed by the user interface engine 170 and display device 156 to display information to the caregiver. Reference is also made to the example caregiver interface 118 shown in FIG. 7.

In some embodiments, color is used by the user interface engine 170 to convey additional information to the caregiver. For example, when a data item 244 is entered into one of the note data displays 240, the user interface engine 170 operates to display the data item 244 with a font color associated with the state of that data item.

The current data item column 262 of the table 260 illustrates one example of the possible colors that can be used by the user interface engine to display the data item 244. In this example, two colors are used to represent the state of the data item. If the state is "normal," the data item 244 is displayed in a first font color, such as blue. If the state is "abnormal," the data item is displayed in a second font color, such as red. Another possible embodiment utilizes "positive" and "negative" state identifiers, rather than "normal" and "abnormal." Other embodiments include other state identifiers. More than two state identifiers and associated colors are used in some embodiments to provide further information. For example, a yellow color can be used to indicate an in-between state. As another example, a relative severity of a finding can be represented by multiple colors or shades of colors. Alternatively, colors can be associated with different groups of findings. For example, a finding relating to a potential heart condition can be displayed in a first color, while a finding relating to a potential infection can be displayed in a second color, and so on.

Additionally, some embodiments utilize colors to display data in controls 242 associated with historical records. For example, in FIG. 7 the caregiver interface 118 displays the date of each historical record in the associated controls 242$^2$ and 242$^3$. The data is displayed in a color. Specifically, the color is determined by determining the state of the data item 242 in that historical record, and then identifying the color associated with that state, such as shown in table 260. The historical control column 264 shows the possible scenarios. When the user interface engine displays a control 242, it determines the state of the data item 244 in the associated historical record. If the state of the data item 244 is normal, then the control is displayed with a first color, such as blue. If the state of the data item 244 is abnormal, then the control is displayed with a second color, such as red.

If the user interface engine 170 determines that there are no historical records associated with the current data item, then historical controls (such as 242² and 242³) are not generated. Accordingly, and as shown in table 264, there is also no color associated with the historical control. However, the absence of a historical control is also used in some embodiments to convey information to the caregiver, as shown in the Information Conveyed column of table 266.

By utilizing colors in this manner, the user interface engine 170 conveys information to the caregiver, such as identified in the Information Conveyed column 266 of table 260. For example, as shown in the first row 268 of table 260, if a current data item 244 is displayed in blue and a historical control 242 is also displayed in blue, the caregiver interface 118 conveys to the caregiver that the patient's condition has not changed significantly. It may also inform the caregiver, for example, that a treatment has not been successful. The second row 270 shows that if a current data item 244 is red, and a historical control 242 is blue, the caregiver interface 118 conveys to the caregiver that the patient's condition has worsened. It may also inform the caregiver, for example, that a treatment has not been successful. The third row 272 shows that if a current data item 244 is displayed in blue and a historical control 242 is displayed in red, the caregiver interface 118 conveys to the caregiver that the patient's condition has improved, and possibly that a treatment has been successful. The fourth row 274 shows that if a current data item 244 is displayed in red, and a historical control 242 is also displayed in red, then the caregiver interface 118 conveys to the caregiver that the patient's condition has not changed substantially. If no historical controls are displayed, as shown in the fifth and sixth rows 276 and 278, the caregiver interface 118 conveys to the caregiver that this finding has not been noted in any of the patient's historical records.

With continued reference to the user interface engine 170, shown in FIG. 3, FIGS. 10-14 illustrate example methods of operating user interface engine 170.

Figure 10:
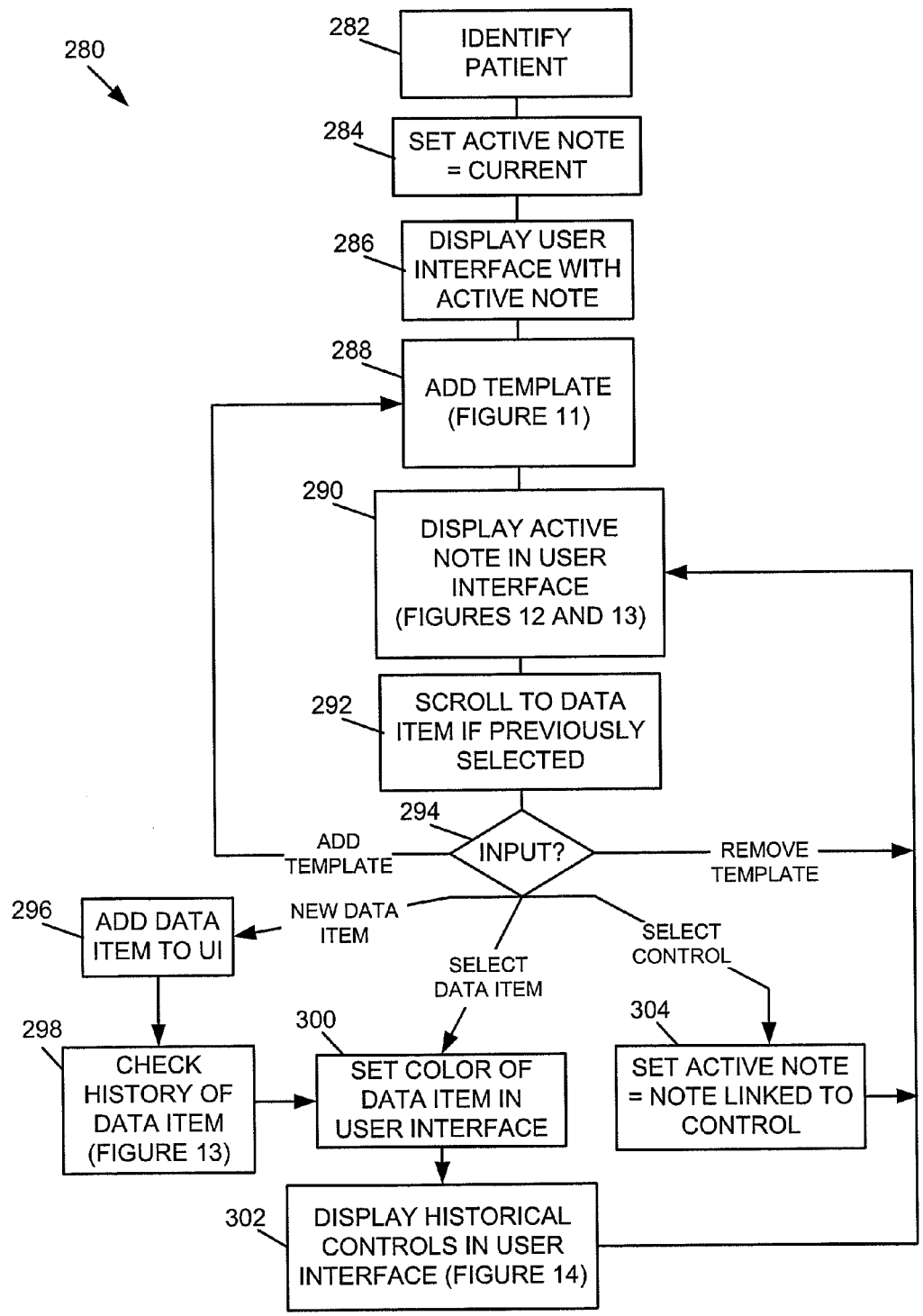
FIG. 10 is a schematic flow chart illustrating an exemplary method of generating a caregiver interface.

FIG. 10 is a flow chart illustrating an exemplary method 280 of operating user interface engine 170 to generate a caregiver interface 118 on display device 156. In some embodiments the method is performed by a processing device 120 utilizing program data stored in memory 122.

The flow chart provides an overview of the operations performed by the user interface engine 170 in an example embodiment. Further details of certain operations are discussed in more detail with reference to FIGS. 11-14, as shown. Further, FIGS. 15-20 illustrate screen shots of an example caregiver interface 118 that is generated by the user interface engine 170 for display on display device 156.

Method 280 begins with an operation 282 in which a caregiver identifies the current patient using caregiver interface 118. In one example embodiment, caregiver interface 118 generates a patient selection window that allows the caregiver to search for and select the current patient. In another possible embodiment, the caregiver utilizes a patient tool of the toolbar 230 (shown in FIG. 7) to select the current patient. Some embodiments include other operations that operate to identify the current patient in the caregiver interface 118.

An operation 284 sets the active note to the current note data display 240¹ (shown in FIG. 7). The operation 284 sets the current note data display 240¹ as the default display to be displayed in the note workspace 232 (shown in FIG. 7) as the active note. The operation 284 is not required in all embodiments, as some embodiments do not include an operation to define an active note, but are configured to automatically display the current note data display 240¹.

An operation 286 operates to display the caregiver interface 118 including the active note. Because the active note was set to be the current note data display 240¹ in the operation 284, the caregiver interface 118 displays the current note data display 240¹.

Figure 15:
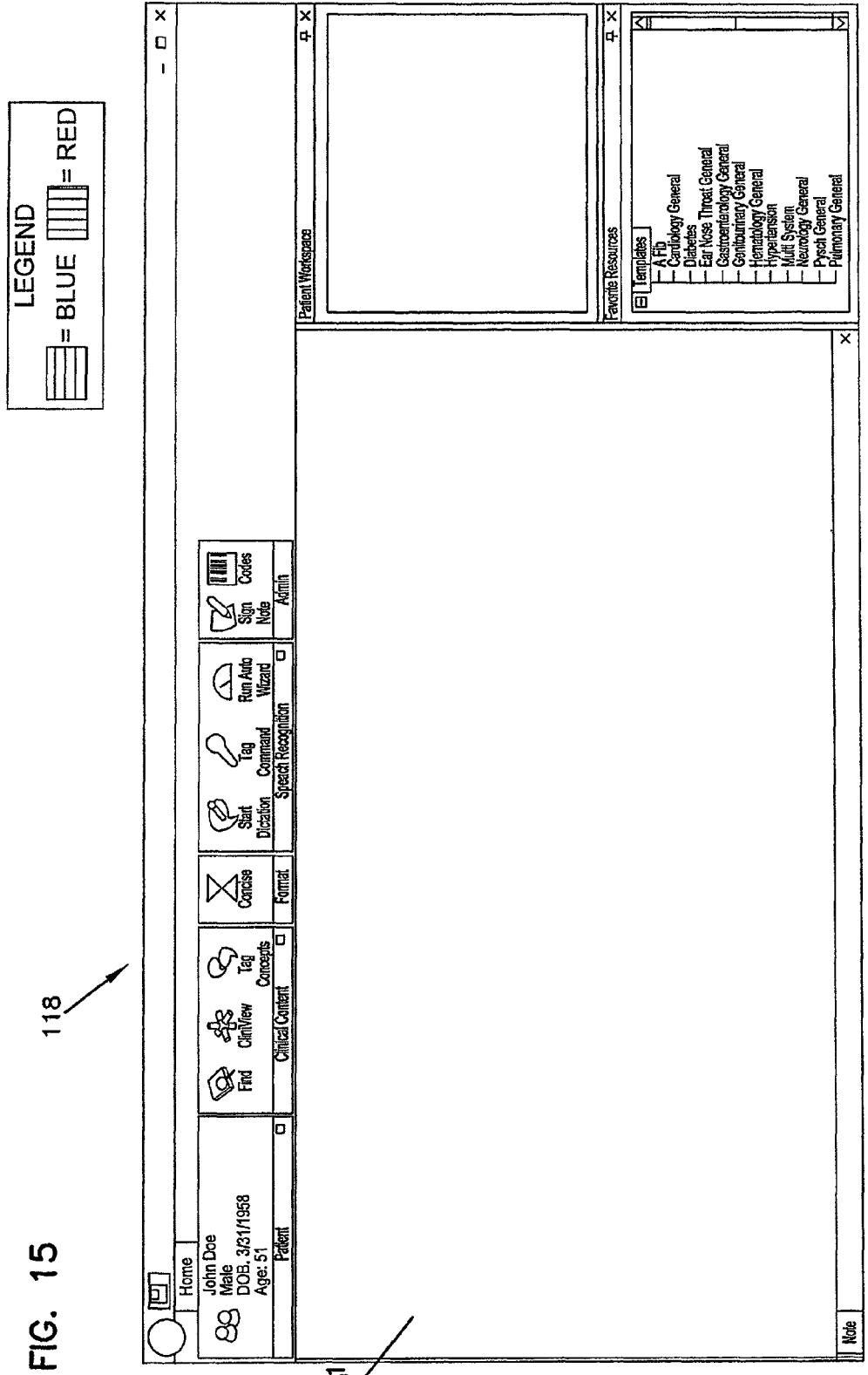
FIG. 15 is a screen shot of an exemplary caregiver user interface.

FIG. 15 illustrates a first screen shot of one example caregiver interface 118 including a blank current note data display 240¹, such as generated in the operation 286 shown in FIG. 10. As shown in FIG. 15, when the current note data display 240¹ is first presented, no information is contained in it. Alternative embodiments, however, do include default information, such as from a default template. In another possible embodiment, the patient's previous historical record is displayed instead of the current note display.

Returning to FIG. 10, an operation 288 is performed to select and add a template from template data 174 (shown in FIG. 3). An exemplary embodiment of the operation 288 is described in more detail below with reference to FIG. 11. The templates typically include a layout that defines an organization for data in current note data display 240¹. In some embodiments the template further includes suggested data items, which are also displayed.

Following the selection of a template, an operation 290 is performed to update the user interface to include the additional template data. An exemplary embodiment of the operation 290 is described in more detail below with reference to FIGS. 12 and 13.

An operation 292 determines whether a data item has been previously selected, and if so, the operation 292 operates to scroll the active note data display 240 to show the selected data item in note workspace 232. In this case, no data item has been previously selected. Accordingly, the operation 292 does not adjust the display. If a data item had been previously selected (such as in the operation 294 discussed below), then the operation 292 operates to automatically scroll the active note data display 240 to the location of the selected data item. This operation improves efficiency by displaying the desired information automatically, without requiring a caregiver to manually scroll through the data in the note data display and without requiring the caregiver to initiate a separate search operation. However, the operation 292 is not included in all embodiments.

Figure 16:
FIG. 16 is another screen shot of the example caregiver user interface shown in FIG. 15.

FIG. 16 illustrates a second screen shot of one example caregiver interface 118, such as displayed after the operation 292 has been performed and while the operation 294 is awaiting input from the caregiver. In this example, a "Collected By Nurse" template 310 is selected in the template selection window 234 (also referred to as the patient workspace). The template data associated with template 310 is displayed in current note data display 240¹. In addition, in this example the caregiver (such as a nurse) has already gathered and entered several findings in data items 244. An exemplary process of adding new data items is described below with reference to an operation 296. The data items 244 include finding 312 of "respiration rate 17 breaths/min", finding 314 of "pulse rate normal 74 bpm", finding 316 of "systolic blood pressure 128 mmHg", and finding 318 of "diastolic blood pressure 86 mmHg."

Returning to FIG. 10, once the caregiver interface 118 has been displayed, an operation 294 is performed to await input from the caregiver. In this example there are several possible inputs, including an input requesting the addition of a new template, an input requesting the removal of a new template, an input entering a new data item, an input selecting a data item, and an input selecting a control.

If the caregiver wants to add an additional template, the caregiver selects the template in the operation 294, which returns method 280 to the operation 288. The additional template is then merged with the previously selected template and displayed in the operation 290.

Figure 17:
FIG. 17 is another screen shot of the example caregiver user interface shown in FIG. 15.

FIG. 17 illustrates another screen shot of an exemplary caregiver interface 118. In this example the caregiver has selected three templates, as shown in the template selection window 234. The selected templates include the previously selected "Collected By Nurse" template, and also includes the "A Fib" template 320 associated with an atrial fibrillation examination, and a cardiology general template 322 associated with a general cardiology examination. Current note data display 240[1] displays the merged templates. In addition, the example shown in FIG. 17 further includes a narrative provided by the caregiver in data entry field 324 that documents the current complaint and in the data entry field 326 that documents the history of the present illness. Some embodiments include a tagging function that operates to identify data items in the narrative and determine whether each identified data item is found in any historical records. Some embodiments further evaluate the state of the data item and display the data item in a color associated with that state.

Returning to FIG. 10, after additional templates have been added, the operation 280 returns to the operation 294 to await input from the caregiver. If the caregiver wants to remove a template, the caregiver provides an input requesting that the template be removed. For example, the caregiver deselects a checkbox associated with the template that should be removed. The operation 290 is then performed to remove the template and to update the caregiver interface 118 accordingly.

Another possible input received from the caregiver in the operation 294 is the entry of a new data item provided to record a finding during the current interaction. When a new data item is entered by the caregiver, an operation 296 is performed to add that data item to caregiver interface 118. In addition, as discussed below, in some embodiments the caregiver interface 118 automatically generates and displays selectable controls in the user interface 118 that are linked to the historical records associated with that finding, when a new finding is added.

After a new data item is entered, an operation 298 is also performed in some embodiments to check the history of the data item in the patient's historical records. If determined in the operation 298 that the data item is in at least one historical record, the data item is displayed in a different font (such as underlined) to visually indicate to the caregiver that the data item was found in the patient's historical records. An example of the operation 298 is described in more detail with reference to FIG. 13. When a new data item is entered, some embodiments operate to automatically select the data item, as if the caregiver had manually selected the new data item. As a result, operations 300 and 302 are performed as discussed below.

Another possible input received in the operation 294 is to select a data item from the active note data display 240 to cause the caregiver interface 118 to provide more information about the selected data item. In an exemplary embodiment, an operation 300 is performed after a data item is selected by the caregiver. As noted above, the operation 300 is similarly performed when a new data item is first entered in the operation 296.

An operation 300 is performed to set the color of a data item in the user interface after the data item has been selected. In some embodiments, the color of the data item shows the state of the data item. In some embodiments, the operation 300 involves determining a state associated with the data item from a state table (such as the state table 196 shown in FIG. 5) and then determining the color associated with that state from a color table (such as the color table 198, also shown in FIG. 5). By displaying the data item in the respective color, the caregiver interface 118 conveys to the caregiver the state of the data item.

An operation 302 is then performed to display historical controls 242 in the caregiver interface 118, if appropriate. If the selected data item is also located in one or more of the patient's historical records, the user interface is updated to include historical controls 242 linked to each of the historical records. An exemplary embodiment of the operation 302 is shown in more detail in FIG. 14.

Additional inputs can be provided in operation 294 to implement any of the operations discussed herein, or additional functions. For example, another possible input that can be provided at operation 294 is to hover over a data item in the caregiver interface 118 with a pointer. In some possible embodiments, when this input is received, the caregiver interface 118 generates and displays a list of historical data records associated with that data item. In some embodiments the date of each historical record is displayed in the list. In an exemplary embodiment, the dates are all identified with the same color font. In another possible embodiment, the dates in the list can be identified with a color to indicate the state of the finding as it was recorded in the note corresponding to that date.

The user can then click on a particular item or date in the list to generate a historical control (such as a tab or other control) corresponding to the note from that date. In an alternative embodiment, clicking on the date causes the user interface to display the note corresponding to the actuated date. In yet another possible embodiment, the list of dates includes a general button the user can actuate to generate tabs for all, or a subset of, the notes corresponding to the dates shown in the list.

Figure 18:
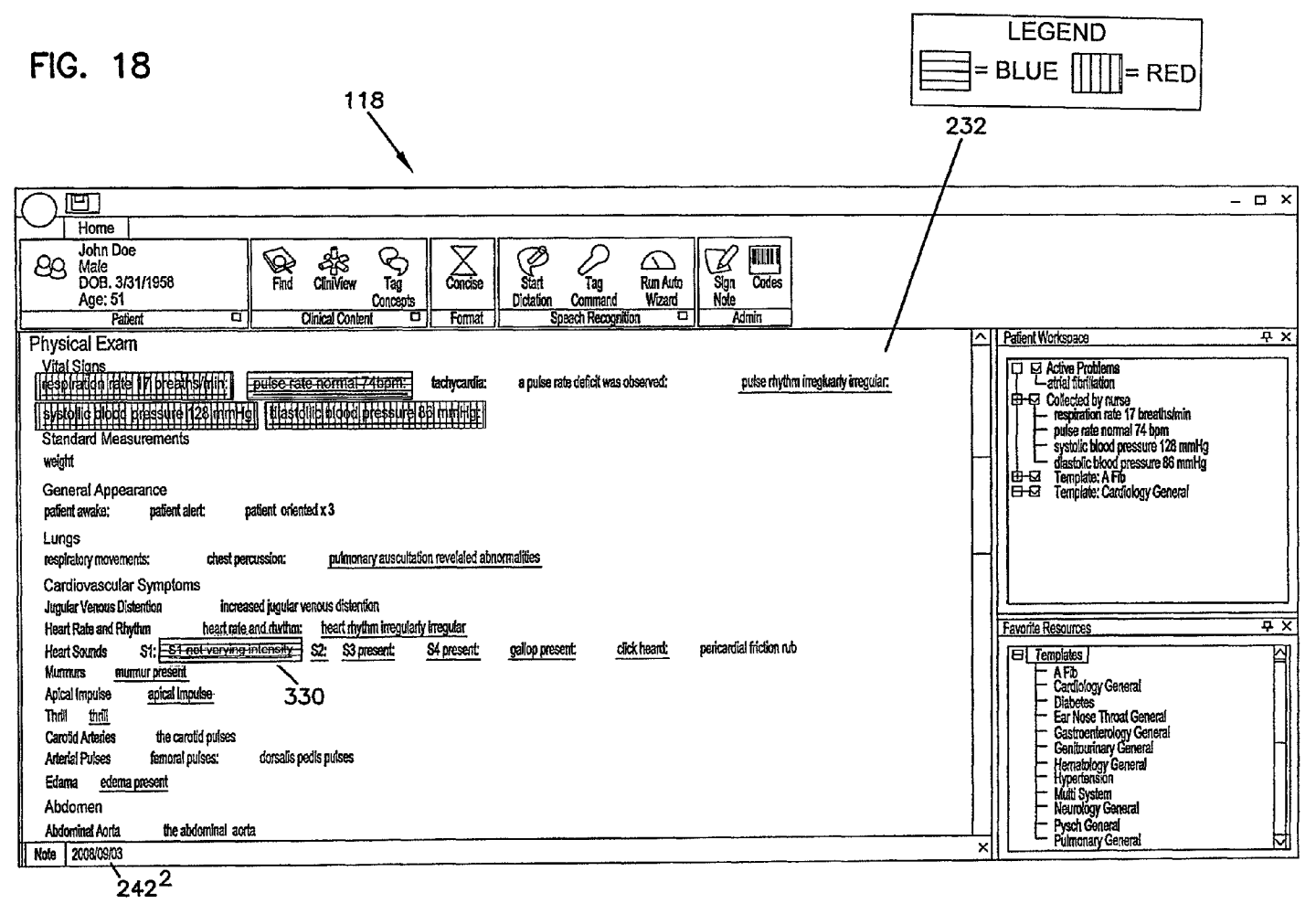

FIG. 18 illustrates another screen shot of an example caregiver interface 118, such as displayed after a caregiver has selected a data item 330 of "S1 not varying intensity" and after operations 300 and 302, shown in FIG. 10, have been performed.

When the caregiver selects a finding, such as by selecting the "S1 not varying intensity" data item 330, the user interface engine 170 displays the finding with a font color associated with the status of that data item 330. In this example, the state associated with a heart sound of "S1 not varying in intensity" is normal, and therefore the data item is displayed in caregiver interface 118 with a blue font color. The color informs the caregiver that the status of the data item is "normal."

Also shown in FIG. 18, after selecting data item 330, historical control 242[2] is displayed. The historical control 242[2] includes the date of the associated historical record (2008/09/03), which is displayed in a red font color. The red color conveys to the caregiver that the finding is associated with an "abnormal" state in that historical note data record. Because the data item 330 is displayed in blue and the date in control 242[2] is displayed in red, the caregiver interface 118 also conveys to the caregiver that the patient's condition has improved.

Returning now to FIG. 10, another possible input received in the operation 294 is a selection of a control 242, such as previously displayed by the operation 302. Each control is linked to a note data display 240. When the control 242 is selected, the operation 304 sets the active note to the note data display 240 associated with the selected control 242. The operation 290 is then performed to update the caregiver interface 118 to display the note data display 240 associated with the selected control 242. In addition, because a data item was previously selected (e.g., S1), the operation 292 is performed to automatically scroll the note data display 240 so that the selected data item is visible in note workspace 232.

Figure 19:
FIG. 19 is another screen shot of the example caregiver user interface shown in FIG. 15.

FIG. 19 illustrates another screen shot of an exemplary caregiver interface 118, such as displayed after a caregiver has selected a control $242^2$. After selection of the control $242^2$, caregiver interface 118 displays the associated historical note data display $240^2$ in note workspace 232. The caregiver interface 118 visually appears to hide the current note data display $240^1$ behind the historical note data display $240^2$, so that only the associated control $242^1$ is visible in note workspace 232. FIG. 19 further shows an example of the operation 292, which operates to automatically scroll the note data display $240^2$ until the selected data item (e.g., S1) is visible in note workspace 232.

Figure 20:
FIG. 20 is another screen shot of the example caregiver user interface shown in FIG. 15.

Similarly, as shown in FIG. 20, if the caregiver desires to return to the current note data display $240^1$, the current control $242^1$ is selected. The caregiver interface 118 is then updated to display the current note data display $240^1$ shown in FIG. 20.

Reference is now made to FIGS. 11-14, which provide further details of example embodiments of the method 280 (shown in FIG. 10) of generating a caregiver interface 118.

Figure 11:
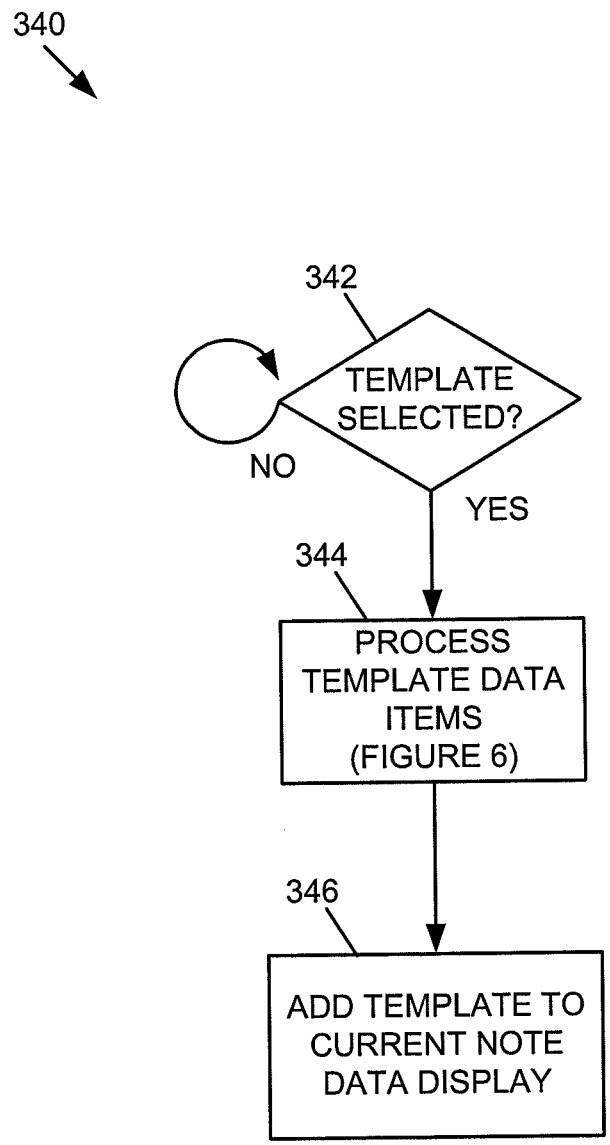
FIG. 11 is a schematic flow chart illustrating an exemplary method of adding a template to a caregiver user interface.

FIG. 11 is a flow chart of an exemplary method 340 of adding a template to a caregiver interface 118, such as performed in the operation 288 of method 280 (shown in FIG. 10). In some embodiments, the method 340 includes operations 342, 344, and 346.

An operation 342 is performed to determine if a template is selected, and continues until a template is selected. For example, a template can be selected by a caregiver by selecting the template from favorite template selection window 236 or by selecting a selectable control 248 associated with a template (see FIG. 7). Other embodiments include other tools for selecting a template. For example, some embodiments receive a voice command identifying the template.

After a template has been selected, an operation 344 is performed to process the template. More specifically, if the template includes suggested data items, each data item of the template is processed to determine if any of the data items are contained in at least one of the patient's historical record. The resulting historical data is then stored as link data 168 that is associated with each data item. An example of operation 344 is method 210 shown in FIG. 6.

An operation 346 is then performed to add the template to the current note data display $240^1$. If multiple templates are selected, the operation 344 further operates to merge the templates into a single merged template. The templates are then displayed in caregiver interface 118.

Figure 12:
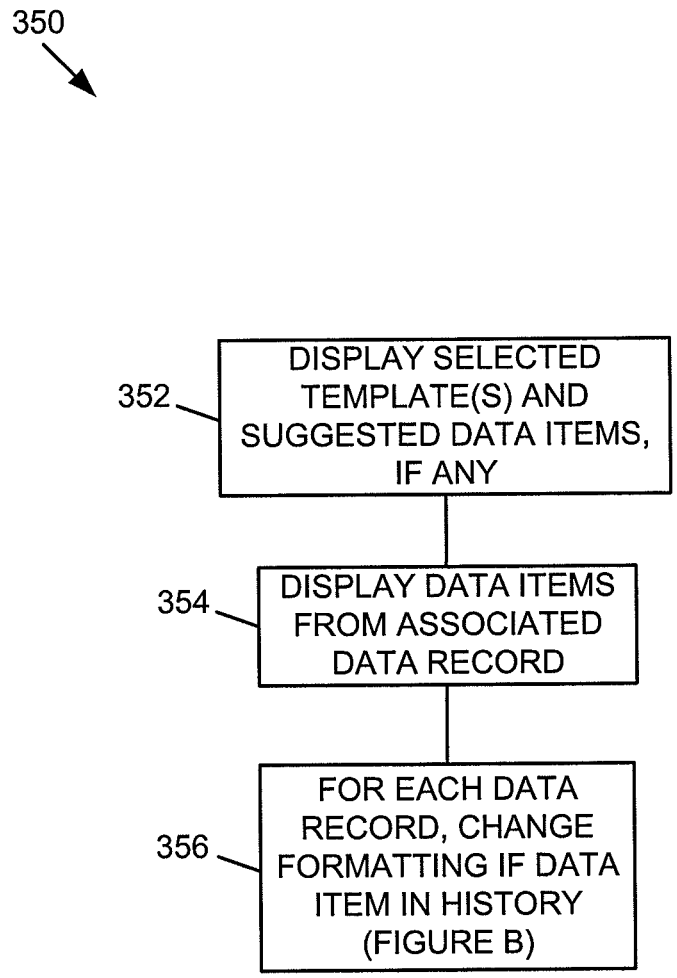
FIG. 12 is a schematic flow chart illustrating an exemplary method of displaying a note data display in a caregiver interface.

FIG. 12 is a flow chart of an exemplary method 350 of displaying a note data display 240 in the caregiver interface 118, such as performed by the operation 290 of method 280 (shown in FIG. 10). In some embodiments, method 350 includes operations 352, 354, and 356.

An operation 352 is performed to display selected templates and suggested data items. The operation 352 determines if any templates have been selected, and if so, displays the template in the note data display 240. As discussed above, an example template is shown in FIG. 7 as displayed in the current note data display $242^1$, and includes finding categories 250 and associated input fields 252. If the template includes suggested data items 244, the suggested data items 244 are also displayed.

An operation 354 is then performed to display data items from the associated data record. For example, if the active note is the current note data display $240^1$, then operation 354 retrieves the data items from current record 176 of program data 142 (shown in FIG. 3) and displays the data items in the current note data display $240^1$. On the other hand, if the active note is a historical note data display $240^2$, then the operation 354 retrieves the data items from the downloaded historical record 164 of program data 142 (shown in FIG. 3) and displays the data items in the active historical note data display $240^2$.

Figure 13:
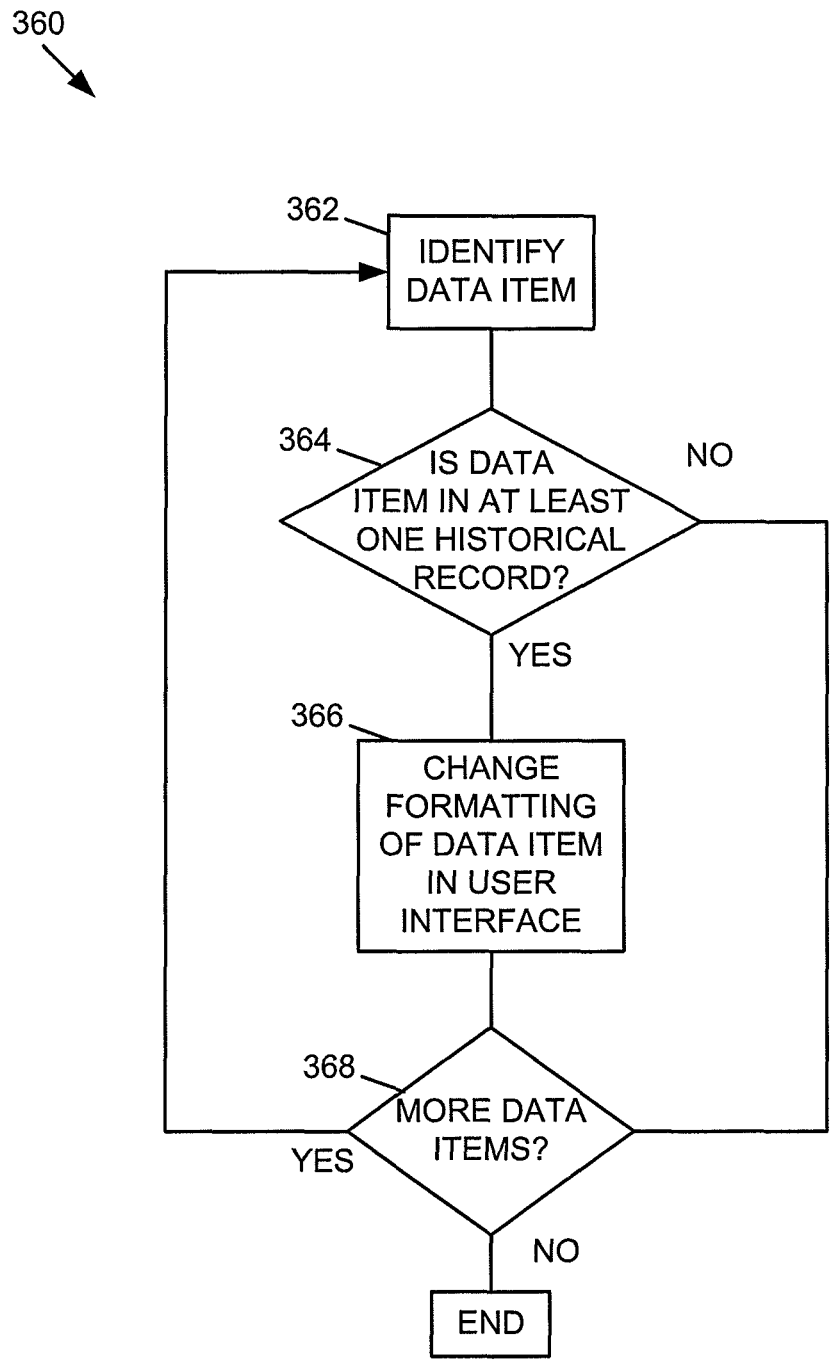
FIG. 13 is a schematic flow chart illustrating an exemplary method of processing data items to set a display format for each data item.

An operation 356 is performed to evaluate each data record to determine if the data record is included in at least one historical record. If so, the operation 356 updates changes the formatting for that data record. For example, in some embodiments all data items that are found in at least one historical record are displayed in a second formatting. An example of a second formatting is an underline. Other formatting is used in other embodiments. A more detailed example of the operation 356 is shown in FIG. 13. In some embodiments the operation 356 is performed for all data items present in a note data display, including both suggested data items provided by a template and entered data items entered by a caregiver.

Some embodiments of method 350 perform the operations 354 and 356 simultaneously so that the data items are only displayed once in the operation 350, with proper formatting, rather than displaying all data items first and then subsequently changing the formatting for historical data items. Further, the operations of method 350 can be performed in any order as desired.

FIG. 13 is a flow chart of an exemplary method 360 of processing data items to set a display format for each data item, such as performed by operation 356 of method 350 (shown in FIG. 12). In some embodiments, method 360 includes operations 362, 364, 366, and 368.

Method 350 begins by identifying a first data item in the operation 362. In one example, the first data item is identified by determining a first data item in a template or in a note data record.

An operation 364 is then performed to determine whether the data item is in at least one of the patient's historical records. If the data item has been previously processed (such as by method 210, shown in FIG. 6), the operation 364 involves checking for link data 168 (shown in FIG. 3) that is associated with the data item. If any historical records are identified in link data 168, then operation 364 results in a "yes" determination and method 360 proceeds to an operation 366. If link data 168 indicates that there are no historical records that contain the data item, then the operation 364 results in a "no" determination and method 360 proceeds to an operation 368. In some embodiments, all historical records containing the data item are identified in operation 364. In another possible embodiment, processing ends as soon as at least one historical record, such as the most recent historical record, is identified that includes the data item. The remaining historical records can then be identified at a later time, if necessary, such as upon selection of the selectable control associated with the data item, or upon selection of a selectable control linked to the historical record.

In some possible embodiments, the historical records are loaded into the program data 142 when they are identified and the links are created. In another possible embodiment, the historical records are not downloaded until a later time, such as when a user activates a link to the historical record.

The operation 366 is performed for each data item that is determined to be a historical data item. For each historical data item, the operation 366 changes the formatting of the data item in the user interface. For example, the historical data item is underlined. Other embodiments change the display in another manner, such as to change the font style, font color, font size. Other possible embodiments display another visually perceptible indication of the historical record in the user interface so that it is associated with the historical data item. In some embodiments the data item is associated with a selectable control, and upon selection of the selectable control, additional selectable controls are displayed that are linked to historical records containing the same data item.

The operation 368 is then performed to determine if there are more data items to be processed. For example, the operation 368 can check a template or a note data item that is currently being processed in the operation 360 to determine if there is another data item after the previously processed data item. If there is another data item, the method 360 returns to the operation 362 to identify the next data item. If there is not another data item, then method 360 ends.

Figure 14:
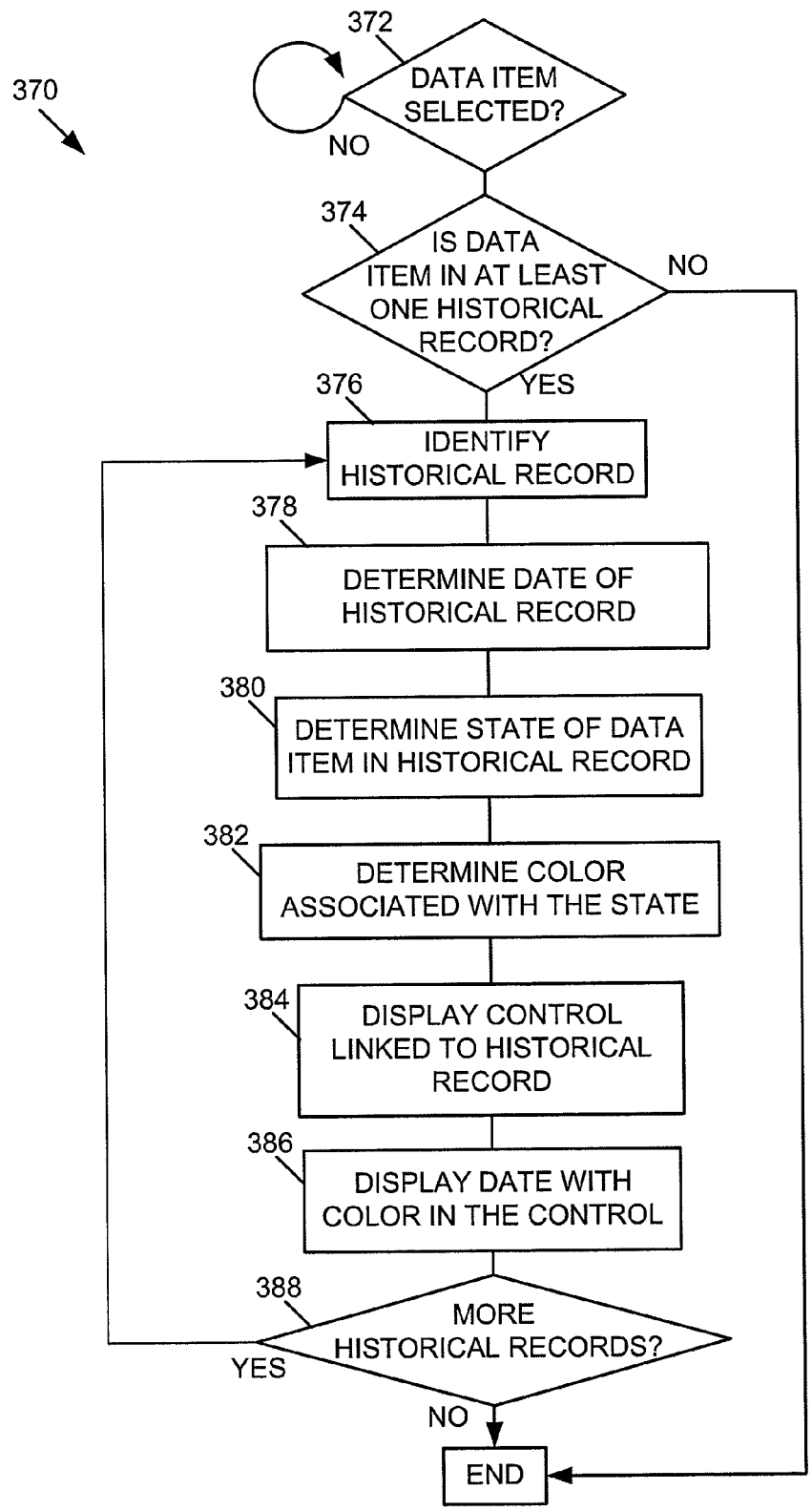
FIG. 14 is a schematic flow chart illustrating an exemplary method of displaying historical controls in the caregiver interface 118.

FIG. 14 is a flow chart of an exemplary method 370 of displaying historical controls in a caregiver interface, such as performed in the operation 302 of method 280 (shown in FIG. 10). In some embodiments, the method 370 includes operations 372, 374, 376, 378, 380, 382, 384, 386, and 388.

An operation 372 is first performed to determine if a data item has been selected. If determined that the data item has not been selected, the operation 372 waits for a data item to be selected. Once the data item is selected, method 370 proceeds to the operation 374. In one example embodiment, selection of a data item involves clicking on the data item with a mouse pointer. In other example embodiments, the data item is selected by the caregiver providing an input through a keyboard, a microphone, a touch sensor, or another input device.

Once a data item is selected, an operation 374 is performed to determine if the data item is in at least one historical record. In some embodiments, the operation 374 checks link data 168 to determine if the data item is linked to any historical records. If the selected data element is not in any historical records, then method 370 ends.

In an alternative embodiment, data elements can not be selected in the operation 372 unless the data element is associated with at least one historical record. In this example, the operation 374 would be redundant and therefore is not included in method 370.

Operations 376, 378, 380, and 382 are next performed to retrieve data associated with the selected data item. In some embodiments, the operations 376, 378, 380, and 382 retrieve data that has previously been identified and stored as link data 168 (shown in FIG. 3). An operation 376 identifies a first historical record associated with the data item. An operation 378 then determines the date of the historical record. An operation 380 then determines the state of the data item in the historical record. An operation 382 then determines the color associated with the state.

An operation 384 is performed to display the control 242 linked to the historical record. One example of a control is a selectable tab. Other embodiments include other selectable controls, such as those described herein or other controls.

An operation 386 is performed to display the date of the historical record, identified in the operation 378, in the historical control using a font color that matches the color identified in the operation 382. The font color conveys to the caregiver the state of the data item in that historical record, which is in some embodiments a physical or mental characteristic of a person. Other embodiments utilize other types of formatting, other than a font color, such as a font type, a font style, or a font size. Yet other embodiments display other visual indicators in caregiver interface 118 to convey the information to the caregiver.

An operation 388 is then performed to determine if there are more historical records that are associated with the selected data item. If so, method 370 returns to operation 376 to identify the next historical record. Otherwise, method 370 ends.

Returning now to FIG. 3, application program 138 further includes a voice recognition engine 178 that processes voice inputs provided by a caregiver. In this example, voice recognition engine 178 receives voice inputs from input/output interface 154. Voice recognition engine 178 utilizes a word base 180, which includes medical vocabulary 182 and non-medical vocabulary, to identify the words input by the caregiver. In one example embodiment, the voice recognition engine 178 is the NUANCE® SpeechMagic™ software application. In some embodiments the voice recognition engine 178 operates to compare an input waveform to a set of word waveforms and to identify the word or words that have the closest match.

In one embodiment the output of the voice recognition engine 178 is either a command or a data entry. Commands are passed to the user interface engine, such as to receive an input and update the user interface. Data entry is passed to the coding engine 186, which compares the data entry to a standardized word base, such as in word base 180. If the data entry is not in the standardized word base, the coding engine 186 checks for synonyms of the data entry. If a synonym is found, the data entry is converted to the standardized word. The data entry is then stored into the current record 176 of program data 142.

In some embodiments, after the current record 176 has been completed, application program 138 uploads the current record 176 to data center 108. Once received by data center 108, the current record 176 becomes a historical data record that can be used in subsequent interactions.

The system and methods disclosed herein, or otherwise falling with the scope of the appended claims, can be adapted to comply with the definition of "Meaningful Use of Certified HER Technology" within The American Recovery and Reinvestment Act of 2009, as well as any statute, regulation, guidelines, and the like.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

The claimed invention is:

1. A method of generating a user interface, the method comprising:
    displaying a note data record in a user interface, the displayed note data record including a data item representing a specific medical finding recorded in the current note data record;
    upon selecting the data item, identifying one or more historical note data records containing the data item;
    generating a data-item selectable control linked to the displayed data item and the identified one or more historical note data records, each of the linked one or more historical note data records containing the data item;
    upon actuation of the data-item selectable control, displaying one or more historical note selectable controls, each historical note selectable control being associated with only a historical note data record that includes the data item, each historical note selectable control being associated with a color indicative of a status of the data item in the associated historical note data record; and upon actuation of one of the displayed historical note selectable controls, displaying at least a portion of the historical note data records related to the actuated historical note selectable control, the display of the historical note data record comprising the data item in a format distinguished from unselected data items.

2. The method of claim 1, further comprising:
receiving an input identifying the data item of the current note data record, wherein receiving an input comprises receiving an entry of a new data item, and wherein generating a data-item selectable control is performed automatically upon entry of the new data item.

3. The method of claim 1, wherein generating a data-item selectable control occurs when the data item is displayed.

4. The method of claim 1, wherein generating a data-item selectable control occurs when a template is loaded that includes the data item as a suggested data item.

5. The method of claim 1, wherein generating a data-item selectable control is performed automatically.

6. The method of claim 1, further comprising:
receiving an input to select at least one of the historical note selectable controls; and
displaying the historical note data record including the data item in the user interface.

7. The method of claim 1, further comprising wherein displaying the historical note selectable control further comprises displaying a date of the historical note data record associated with the selectable control.

8. The method of claim 1 wherein displaying the data item comprises displaying the data item in at least one font selected from the group consisting essentially of: underline, bold, and italics.

9. The method of claim 1 wherein identifying one or more historical note data records containing the data item occurs before generating a data-item selectable control linked to the displayed data item and the identified one or more historical note data records.

10. The method of claim 1 wherein the act of displaying the data item in a user interface occurs after the act of identifying one or more historical note records containing a data item.

11. The method of claim 1 wherein generating a data-item selectable control occurs upon selecting the data item.

12. The method of claim 1 wherein generating a data-item selectable control occurs upon entering data corresponding to the data item.

13. The method of claim 7, wherein displaying the date further comprises:
determining a state of the data item in the historical note data record.

14. The method of claim 13, wherein visually indicating the state comprises displaying the date with a font color associated with the state.

15. A method of generating a user interface, the method comprising:
displaying a user interface having a first note data record in a first frame, the first note data record including a data item;
receiving an input identifying the data item of the first note data record, the data item representing a specific medical finding associated with a patient and recorded in the first note data record;
determining whether the data item is included in a second note data record;
upon determining whether the data item is included in a second note data record, generating a selectable control linked to the data item and the second note data record;
displaying the selectable control in the first frame while the first note data record is being displayed in the first frame, the selectable control being associated with a color indicative of a status of the data item in the second note data record; and
upon activation of the selectable control, displaying the second note data record, the data item in the second note record being displayed in a format distinguished from other data items.

16. The method of claim 15 wherein receiving an input comprises receiving an entry of a new data item.

17. The method of claim 15 wherein receiving an input comprises identifying a previously entered data item.

18. A method comprising:
identifying a medical finding associated with a patient;
in response to identifying a medical finding, generating a data item identifying the medical finding associated with the patient;
displaying the data item in a user interface;
storing the data item in a first note data record of a data storage device;
identifying historical note data records containing the data item;
upon identifying one or more historical note data records containing the data item:
generating link data, the link data linking the first note data record and the identified historical note data records;
generating a data-item selectable control linked to the displayed data item and the identified one or more historical note data records, each of the linked one or more historical note data records containing the data item; and
changing the font of the data item displayed in the user interface;
upon actuation of the data-item selectable control, displaying one or more note selectable controls, each note selectable control being associated with only a historical note data record that includes the data item and being associated with a color indicative of a status of the data item in the associated historical note data record; and
upon actuation of one of the displayed historical note selectable controls, displaying at least a portion of the historical note data records related to the actuated historical note selectable control, the display of the historical note data record comprising the data item in a format distinguished from unselected data items.

19. The method of claim 18 wherein changing the font of the data item displayed in the user interface comprises changing the font to at least one font selected from the group consisting of: an underline, bold, italics, a different color, a different size, and a different typeface.

20. The method of claim 18 wherein identifying a medical finding associated with a patient comprises receiving an input and the input identifies the medical finding associated with the patient.

* * * * *